(12) United States Patent
Lashinski et al.

(10) Patent No.: US 7,641,686 B2
(45) Date of Patent: Jan. 5, 2010

(54) PERCUTANEOUS HEART VALVE WITH STENTLESS SUPPORT

(75) Inventors: Randall T. Lashinski, Santa Rosa, CA (US); Gordon B. Bishop, Santa Rosa, CA (US)

(73) Assignee: Direct Flow Medical, Inc., Santa Rosa, CA (US)

( * ) Notice: Subject to any disclaimer, the term of this patent is extended or adjusted under 35 U.S.C. 154(b) by 73 days.

(21) Appl. No.: 11/112,847

(22) Filed: Apr. 22, 2005

(65) Prior Publication Data

US 2005/0273160 A1 Dec. 8, 2005

Related U.S. Application Data

(60) Provisional application No. 60/564,708, filed on Apr. 23, 2004, provisional application No. 60/568,402, filed on May 5, 2004, provisional application No. 60/572,561, filed on May 19, 2004, provisional application No. 60/581,664, filed on Jun. 21, 2004, provisional application No. 60/586,054, filed on Jul. 7, 2004, provisional application No. 60/586,110, filed on Jul. 7, 2004, provisional application No. 60/586,005, filed on Jul. 7, 2004, provisional application No. 60/586,002, filed on Jul. 7, 2004, provisional application No. 60/586,055, filed on Jul. 7, 2004, provisional application No. 60/586,006, filed on Jul. 7, 2004, provisional application No. 60/588,106, filed on Jul. 15, 2004, provisional application No. 60/603,324, filed on Aug. 20, 2004, provisional application No. 60/605,204, filed on Aug. 27, 2004, provisional application No. 60/610,269, filed on Sep. 16, 2004.

(51) Int. Cl.
A61F 2/24 (2006.01)

(52) U.S. Cl. ...................... 623/2.1; 623/1.26

(58) Field of Classification Search ................ 623/1.25, 623/2.22, 2.1, 1.26, 1.35, 1.51, 1.53, 1.54
See application file for complete search history.

(56) References Cited

U.S. PATENT DOCUMENTS 3,416,562 A 12/1968 Freeman et al.

(Continued)

FOREIGN PATENT DOCUMENTS

DE 2700531 C2 4/1985

(Continued)

OTHER PUBLICATIONS

International Search Report for PCT Application No. PCT/US2005/015617 (the PCT counterpart of the parent application) filed May 5, 2005.

(Continued)

*Primary Examiner*—David Isabella
*Assistant Examiner*—Suba Ganesan
(74) *Attorney, Agent, or Firm*—Knobbe, Martens, Olson & Bear, LLP.

(57) ABSTRACT

An implantable prosthetic valve having a stentless support structure. The valve has a tubular annular support structure with a first inflatable ring at a proximal end, a second inflatable ring at a distal end, and an inflatable intermediate support in between the first and second inflatable rings. There is at least one moveable occluder that controls the flow of blood through the tubular support structure. The tubular support structure can be filled with inflation media in the first inflatable ring, the second inflatable ring and inflatable intermediate support structure to convert the tubular support structure from a collapsed configuration to a patent tubular configuration.

5 Claims, 17 Drawing Sheets

U.S. PATENT DOCUMENTS

| | | | |
|---|---|---|---|
| 3,657,744 A | 4/1972 | Ersek | |
| 3,671,979 A | 6/1972 | Moulopoulos | |
| 3,714,671 A | 2/1973 | Edwards et al. | |
| 4,035,849 A | 7/1977 | Angell et al. | |
| 4,056,854 A | 11/1977 | Boretos et al. | |
| 4,106,129 A | 8/1978 | Carpentier et al. | |
| 4,183,102 A | 1/1980 | Guiset | |
| 4,339,831 A | 7/1982 | Johnson | |
| 4,592,340 A | 6/1986 | Boyles | |
| 4,612,011 A | 9/1986 | Kautzky | |
| 4,662,885 A | 5/1987 | DiPisa, Jr. | |
| 4,727,873 A | 3/1988 | Mobin-Uddin | |
| 4,750,488 A | 6/1988 | Wuchinich et al. | |
| 4,750,901 A | 6/1988 | Molteno | |
| 4,787,899 A | 11/1988 | Lazarus | |
| 4,817,600 A | 4/1989 | Herms et al. | |
| 4,827,911 A | 5/1989 | Broadwin et al. | |
| 4,892,541 A | 1/1990 | Alonso | |
| 4,922,902 A | 5/1990 | Wuchinich et al. | |
| 4,931,047 A | 6/1990 | Broadwin et al. | |
| 4,960,424 A | 10/1990 | Grooters | |
| 4,994,077 A | 2/1991 | Dobben | |
| 5,015,227 A | 5/1991 | Broadwin et al. | |
| 5,026,383 A | 6/1991 | Nobles | |
| 5,032,128 A | 7/1991 | Alonso | |
| 5,163,897 A | 11/1992 | Persky | |
| 5,163,953 A | 11/1992 | Vince | |
| 5,167,628 A | 12/1992 | Boyles | |
| 5,207,695 A | 5/1993 | Trout, III | |
| 5,360,444 A | 11/1994 | Kusuhara | |
| 5,370,685 A | 12/1994 | Stevens | |
| 5,370,691 A | 12/1994 | Samson | |
| 5,397,351 A | 3/1995 | Pavcnik et al. | |
| 5,411,552 A | 5/1995 | Andersen et al. | |
| 5,423,851 A | 6/1995 | Samuels | |
| 5,443,499 A | 8/1995 | Schmitt | |
| 5,449,385 A | 9/1995 | Religa et al. | |
| 5,500,014 A * | 3/1996 | Quijano et al. | 623/1.24 |
| 5,554,185 A | 9/1996 | Block et al. | |
| 5,616,149 A | 4/1997 | Barath | |
| 5,649,978 A | 7/1997 | Samson | |
| 5,690,570 A | 11/1997 | Chang et al. | |
| 5,817,102 A | 10/1998 | Johnson et al. | |
| 5,840,081 A | 11/1998 | Andersen et al. | |
| 5,848,964 A | 12/1998 | Samuels | |
| 5,855,601 A | 1/1999 | Bessler et al. | |
| 5,871,537 A * | 2/1999 | Holman et al. | 623/1.23 |
| 5,957,949 A | 9/1999 | Leonhardt et al. | |
| 5,980,570 A | 11/1999 | Simpson | |
| 6,007,575 A | 12/1999 | Samuels et al. | |
| 6,090,139 A | 7/2000 | Lemelson | |
| 6,102,944 A | 8/2000 | Huynh et al. | |
| 6,110,201 A * | 8/2000 | Quijano et al. | 623/2.1 |
| 6,117,106 A | 9/2000 | Wasicek et al. | |
| 6,126,007 A | 10/2000 | Kari et al. | |
| 6,168,614 B1 | 1/2001 | Andersen et al. | |
| 6,196,996 B1 | 3/2001 | Teirstein | |
| 6,221,096 B1 | 4/2001 | Aiba et al. | |
| 6,280,412 B1 | 8/2001 | Pederson, Jr. et al. | |
| 6,299,637 B1 | 10/2001 | Shaolian et al. | |
| 6,309,399 B1 | 10/2001 | Barbut et al. | |
| 6,312,465 B1 | 11/2001 | Griffin et al. | |
| 6,371,970 B1 | 4/2002 | Khosravi et al. | |
| 6,371,983 B1 | 4/2002 | Lane | |
| 6,395,019 B2 | 5/2002 | Chobotov | |
| 6,409,759 B1 | 6/2002 | Peredo | |
| 6,425,916 B1 | 7/2002 | Garrison et al. | |
| 6,440,164 B1 | 8/2002 | Dimatteo et al. | |
| 6,458,156 B1 | 10/2002 | Wan et al. | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,544,291 B2 | 4/2003 | Taylor | |
| 6,562,069 B2 | 5/2003 | Cai et al. | |
| 6,572,652 B2 | 6/2003 | Shaknovich | |
| 6,582,462 B1 | 6/2003 | Andersen et al. | |
| 6,602,286 B1 | 8/2003 | Strecker | |
| 6,676,698 B2 | 1/2004 | McGuckin, Jr. et al. | |
| 6,682,543 B2 | 1/2004 | Barbut et al. | |
| 6,692,512 B2 | 2/2004 | Jang | |
| 6,719,788 B2 | 4/2004 | Cox | |
| 6,719,789 B2 | 4/2004 | Cox | |
| 6,733,525 B2 | 5/2004 | Yang et al. | |
| 6,736,845 B2 | 5/2004 | Marquez et al. | |
| 6,755,811 B1 | 6/2004 | Constantz | |
| 6,761,733 B2 | 7/2004 | Chobotov et al. | |
| 6,764,494 B2 | 7/2004 | Menz et al. | |
| 6,767,362 B2 | 7/2004 | Schreck | |
| 6,769,434 B2 | 8/2004 | Liddicoat et al. | |
| 6,890,353 B2 | 5/2005 | Cohn et al. | |
| 6,936,057 B1 | 8/2005 | Nobles | |
| 6,949,122 B2 | 9/2005 | Adams et al. | |
| 6,958,212 B1 | 10/2005 | Hubbell et al. | |
| 6,974,476 B2 | 12/2005 | McGuckin, Jr. et al. | |
| 6,989,027 B2 | 1/2006 | Allen et al. | |
| 6,994,093 B2 | 2/2006 | Murphy et al. | |
| 7,018,406 B2 | 3/2006 | Seguin et al. | |
| 7,037,334 B1 | 5/2006 | Hlavka et al. | |
| 7,052,487 B2 | 5/2006 | Cohn et al. | |
| 7,077,862 B2 | 7/2006 | Vidlund et al. | |
| 7,081,129 B2 | 7/2006 | Chobotov | |
| 7,112,219 B2 | 9/2006 | Vidlund et al. | |
| 7,186,264 B2 | 3/2007 | Liddicoat et al. | |
| 7,201,772 B2 | 4/2007 | Schwammenthal et al. | |
| 7,217,287 B2 | 5/2007 | Wilson et al. | |
| 7,429,269 B2 | 9/2008 | Schwammenthal et al. | |
| 7,442,204 B2 | 10/2008 | Schwammenthal et al. | |
| 2001/0007956 A1 | 7/2001 | Letac et al. | |
| 2001/0021872 A1 | 9/2001 | Bailey et al. | |
| 2002/0082689 A1 | 6/2002 | Chinn | |
| 2002/0095116 A1 | 7/2002 | Strecter | |
| 2002/0123802 A1 | 9/2002 | Snyders | |
| 2002/0151961 A1 | 10/2002 | Lashinski et al. | |
| 2002/0151970 A1 | 10/2002 | Garrison et al. | |
| 2002/0183838 A1 | 12/2002 | Liddicoat et al. | |
| 2002/0183841 A1 | 12/2002 | Cohn et al. | |
| 2003/0023300 A1 | 1/2003 | Bailey et al. | |
| 2003/0023303 A1 | 1/2003 | Palmaz et al. | |
| 2003/0027332 A1 | 2/2003 | Lafrance et al. | |
| 2003/0036795 A1 | 2/2003 | Andersen et al. | |
| 2003/0040772 A1 | 2/2003 | Hyodoh et al. | |
| 2003/0055496 A1 | 3/2003 | Cai et al. | |
| 2003/0078654 A1 | 4/2003 | Taylor et al. | |
| 2003/0083538 A1 | 5/2003 | Adams et al. | |
| 2003/0093145 A1 | 5/2003 | Lawrence-Brown et al. | |
| 2003/0125793 A1 | 7/2003 | Vesely | |
| 2003/0125797 A1 | 7/2003 | Chobotov et al. | |
| 2003/0130730 A1 | 7/2003 | Cohn et al. | |
| 2003/0130731 A1 | 7/2003 | Vidlund et al. | |
| 2003/0191527 A1 | 10/2003 | Shaknovich | |
| 2003/0220684 A1 | 11/2003 | Holman et al. | |
| 2003/0225453 A1 | 12/2003 | Murch | |
| 2003/0233022 A1 | 12/2003 | Vidlund et al. | |
| 2004/0003819 A1 | 1/2004 | St. Goar et al. | |
| 2004/0030381 A1 | 2/2004 | Shu | |
| 2004/0030382 A1 | 2/2004 | St. Goar et al. | |
| 2004/0034320 A1 | 2/2004 | Burnett | |
| 2004/0039442 A1 | 2/2004 | St. Goar et al. | |
| 2004/0087975 A1 | 5/2004 | Lucatero et al. | |
| 2004/0093060 A1 | 5/2004 | Seguin et al. | |
| 2004/0116951 A1 | 6/2004 | Rosengart | |
| 2004/0127979 A1 | 7/2004 | Wilson et al. | |
| 2004/0148019 A1 | 7/2004 | Vidlund et al. | |
| 2004/0148020 A1 | 7/2004 | Vidlund et al. | |

| | | |
|---|---|---|
| 2004/0167620 A1 | 8/2004 | Ortiz et al. |
| 2004/0176836 A1 | 9/2004 | Kari et al. |
| 2004/0186563 A1 | 9/2004 | Lobbi |
| 2004/0210304 A1 | 10/2004 | Seguin et al. |
| 2004/0225354 A1* | 11/2004 | Allen et al. ............... 623/2.11 |
| 2004/0249413 A1 | 12/2004 | Allen et al. |
| 2004/0249452 A1 | 12/2004 | Adams et al. |
| 2004/0254600 A1 | 12/2004 | Zarbatany et al. |
| 2004/0260322 A1 | 12/2004 | Rudko et al. |
| 2004/0260390 A1 | 12/2004 | Sarac et al. |
| 2005/0010285 A1 | 1/2005 | Lambrecht et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0055082 A1 | 3/2005 | Ben Muvhar et al. |
| 2005/0065550 A1 | 3/2005 | Starksen et al. |
| 2005/0090846 A1 | 4/2005 | Pedersen et al. |
| 2005/0107810 A1 | 5/2005 | Morales et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0203549 A1 | 9/2005 | Realyvasquez |
| 2005/0203614 A1 | 9/2005 | Forster et al. |
| 2005/0209674 A1 | 9/2005 | Kutscher et al. |
| 2005/0222488 A1 | 10/2005 | Rahdert et al. |
| 2005/0222489 A1 | 10/2005 | Rahdert et al. |
| 2005/0228422 A1 | 10/2005 | Rahdert et al. |
| 2005/0267574 A1 | 12/2005 | Cohn et al. |
| 2005/0273160 A1 | 12/2005 | Lashinski et al. |
| 2006/0004442 A1 | 1/2006 | Spenser et al. |
| 2006/0020327 A1 | 1/2006 | Lashinski et al. |
| 2006/0020332 A1 | 1/2006 | Lashinski et al. |
| 2006/0020333 A1 | 1/2006 | Lashinski et al. |
| 2006/0020334 A1 | 1/2006 | Lashinski et al. |
| 2006/0025750 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0041306 A1 | 2/2006 | Vidlund et al. |
| 2006/0063970 A1 | 3/2006 | Raman et al. |
| 2006/0074485 A1 | 4/2006 | Realyvasquez |
| 2006/0100699 A1 | 5/2006 | Vidlund et al. |
| 2006/0106449 A1 | 5/2006 | Ben Muvhar |
| 2006/0106450 A1 | 5/2006 | Ben Muvhar |
| 2006/0129025 A1 | 6/2006 | Levine et al. |
| 2006/0129051 A1 | 6/2006 | Rowe et al. |
| 2006/0129235 A1 | 6/2006 | Seguin et al. |
| 2006/0149135 A1 | 7/2006 | Paz |
| 2006/0178700 A1 | 8/2006 | Quinn |
| 2006/0190030 A1 | 8/2006 | To et al. |
| 2006/0217637 A1 | 9/2006 | Leiboff et al. |
| 2006/0229717 A1 | 10/2006 | Cohn et al. |
| 2006/0235512 A1 | 10/2006 | Osborne et al. |
| 2006/0241656 A1 | 10/2006 | Starksen et al. |
| 2006/0252984 A1 | 11/2006 | Rahdert et al. |
| 2006/0271172 A1 | 11/2006 | Tehrani |
| 2006/0276874 A1 | 12/2006 | Wilson et al. |
| 2007/0005133 A1 | 1/2007 | Lashinski et al. |
| 2007/0027536 A1 | 2/2007 | Mihaljevic |
| 2007/0038293 A1 | 2/2007 | St.Goar et al. |
| 2007/0043435 A1 | 2/2007 | Seguin et al. |
| 2007/0050022 A1 | 3/2007 | Vidlund et al. |
| 2007/0142906 A1 | 6/2007 | Figulla et al. |
| 2007/0185566 A1 | 8/2007 | Khitin et al. |
| 2007/0203575 A1 | 8/2007 | Forster et al. |
| 2009/0082857 A1 | 3/2009 | Lashinski et al. |

FOREIGN PATENT DOCUMENTS

| | | |
|---|---|---|
| WO | WO 91/17720 | 11/1991 |
| WO | WO 93/01768 | 2/1993 |
| WO | WO 96/02212 | 2/1996 |
| WO | WO 00/41652 | 7/2000 |
| WO | WO 03/096932 A1 | 11/2003 |
| WO | WO 2005/087140 A1 | 9/2005 |
| WO | 2005/107650 A2 | 11/2005 |

OTHER PUBLICATIONS

Written Opinion of the International Searching Authority for Application No. PCT/US2005/015617 (the PCT counterpart of the parent application) filed May 5, 2005.

U.S. Appl. No. 11/579,723, our reference: including its prosecution history, Lashinski, et al.

Extended Search Report dated Nov. 17, 2008 for Applicant's European App. No. 06772431.0 in 6 pages.

U.S. Appl. No. 09/496,231, Jeffrey A. Hubbell et al., Biomaterials Formed by Nucleophilic Addition Reaction to Conjugated Unsaturated Groups, filed on Feb. 1, 2000.

European Search Opinion for Application No. EP06772431 filed Jun. 7, 2006, dated Nov. 6, 2008, in 3 pages.

Supplementary European Search Report for Application No. EP06772431 filed on Jun. 7, 2006, dated Nov. 6, 2008, in 2 pages.

David et al., Aortic Valve Replacement with the Toronto SPV Bioprosthesis, The Journal of Heart Valve Disease, 1992, pp. 244-248, vol. 1(2), ICR Publishers.

Vyavahare et al., Prevention of Bioprosthetic Heart Valve Calcification by Ethanol Preincubation, Circulation, Jan. 21, 1997, pp. 479-488, vol. 95(2), American Heart Association.

* cited by examiner

PERCUTANEOUS HEART VALVE WITH STENTLESS SUPPORT

CROSS-REFERENCE TO RELATED APPLICATIONS

This application claims priority under 35 U.S.C. § 119 to U.S. Provisional Patent Application Ser. No. 60/564,708, filed Apr. 23, 2004, the disclosure of which is incorporated in its entirety herein by reference. This application additionally claims the priority benefit of (1) U.S. Provisional Application 60/568,402, filed May 5, 2004, (2) U.S. Provisional Application 60/572,561, filed May 19, 2004, (3) U.S. Provisional Application 60/581,664, filed Jun. 21, 2004, (4) U.S. Provisional Application 60/586,054, filed Jul. 7, 2004, (5) U.S. Provisional Application 60/586,110, filed Jul. 7, 2004, (6) U.S. Provisional Application 60/586,005, filed Jul. 7, 2004, (7) U.S. Provisional Application 60/586,002, filed Jul. 7, 2004, (8) U.S. Provisional Application 60/586,055, filed Jul. 7, 2004, (9) U.S. Provisional Application 60/586,006, filed Jul. 7, 2004, (10) U.S. Provisional Application 60/588,106, filed Jul. 15, 2004, U.S. Provisional Application 60/603,324, filed Aug. 20, 2004, (11) U.S. Provisional Application 60/605,204, filed Aug. 27, 2004 and (12) U.S. Provisional Application 60/610,269 filed Sep. 16, 2004, the entire contents of which are hereby expressly incorporated by reference herein.

BACKGROUND OF THE INVENTION

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

A need therefore remains for methods and devices for treating mitral valvular insufficiency, which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices.

The circulatory system is a closed loop bed of arterial and venous vessels supplying oxygen and nutrients to the body extremities through capillary beds. The driver of the system is the heart providing correct pressures to the circulatory system and regulating flow volumes as the body demands. Deoxygenated blood enters heart first through the right atrium and is allowed to the right ventrical through the tricuspid valve. Once in the right ventrical, the heart delivers this blood through the pulmonary valve and to the lungs for a gaseous exchange of oxygen. The circulatory pressures carry this blood back to the heart via the pulmonary veins and into the left atrium. Filling of the left ventricle occurs as the mitral valve opens allowing blood to be drawn into the left ventrical for expulsion through the aortic valve and on to the body extremities. When the heart fails to continuously produce normal flow and pressures, a disease commonly referred to as heart failure occurs.

Heart failure simply defined is the inability for the heart to produce output sufficient to demand. Mechanical complications of heart failure include free-wall rupture, septal-rupture, papillary wall rupture or dysfunction aortic insufficiency and tamponade. Mitral, aortic or pulmonary valve disorders lead to a host of other conditions and complications exacerbating heart failure further. Other disorders include coronary disease, hypertension, and a diverse group of muscle diseases referred to as cardiomyopothies. Because of this syndrome establishes a number of cycles, heart failure begets more heart failure.

Heart failure as defined by the New York Heart Association in a functional classification.

Patients with cardiac disease but without resulting limitations of physical activity. Ordinary physical activity does not cause undue fatigue, palpitation, dyspnea, or anginal pain.

Patient with cardiac disease resulting in slight limitation of physical activity. These patients are comfortable at rest. Ordinary physical activity results in fatigue, palpitation, dyspnea, or anginal pain.

Patients with cardiac disease resulting in marked limitation of physical activity. These patients are comfortable at rest. Less than ordinary physical activity causes fatigue palpitation, dyspnea, or anginal pain.

Patients with cardiac disease resulting in inability to carry on any physical activity without discomfort. Symptoms of cardiac insufficiency or of the anginal syndrome may be present even at rest. If any physical activity is undertaken, discomfort is increased.

Congestive heart failure is described as circulatory congestion including peripheral edema. The major factor in cardiac pulmonary edema is the pulmonary capillary pressure. There are no native valves between the lungs and the left atrium therefore fluctuations in left atrial pressure are reflected retrograde into the pulmonary vasculature. These elevations in pressure do cause pulmonary congestion. When the heart, specifically the mitral valve, is operating normally correct flow and pressures throughout the circulatory system are maintained. As heart failure begins these pressures and flow rates decrease or increase depending upon the disease and vascular location.

Placement of valves between the lung and the left atrium will prevent retrograde flow and undesired pressure fluctuations to the pulmonary vasculature. Mechanical valves may be constructed of conventional materials such as stainless steel, nickel-titanium, cobalt-chromium or other metallic based alloys. Other materials used are biocompatible-based polymers and may include polycarbonate, silicone, pebax, polyethylene, polypropylene or floropolymers such as Teflon. Mechanical valves may be coated or encapsulated with polymers for drug coating applications or favorable biocompatibility results.

There are many styles of mechanical valves that utilize both polymer and metallic materials. These include single leaflet, double leaflet, ball and cage style, slit-type and emulated polymer tricuspid valves. Though many forms of valves exist, the function of the valve is to control flow through a conduit or chamber. Each style will be best suited to the application or location in the body it was designed for.

Bioprosthetic heart valves comprise valve leaflets formed of flexible biological material. Bioprosthetic valve or components from human donors are referred to as homografts and xenografts are from non-human animal donors. These valves as a group are known as tissue valves. This tissue may include donor valve leaflets or other biological materials such as bovine pericardium. The leaflets are sewn into place and to each other to create a new valve structure. This structure may be attached to a second structure such as a stent or cage for implantation to the body conduit.

DESCRIPTION OF THE RELATED ART

The concept of placing a percutaneous valve in the pulmonary veins was first disclosed by Block et all in 5,554,185. A specific windsock valve for this application was later described by Shaknovich in U.S. Pat. No. 6,572,652.

SUMMARY OF THE INVENTION

There is provided in accordance with one aspect of the present invention, a flow controlled device dimensioned for implantation in a human pulmonary vein. The device comprises an inflatable support structure in at least one movable occluder that controls the flow of blood into and out of the pulmonary veins. Implantation of the valve between the left atrium and the lung within the pulmonary vein reduces the likelihood and/or the severity of regurgitant flow increasing the pulmonary pressure which may lead to pulmonary edema and congestion.

In accordance with a further aspect of the present invention, a method of monitoring a patient comprises monitoring blood flow through the pulmonary veins during the implantation of the device of Claim 1. In accordance with a further aspect of the present invention, there is provided a method of monitoring blood pressure comprising monitoring blood pressure through the pulmonary veins during the implantation of the pulmonary vein valve.

In accordance with a further aspect of the present invention, there is provided a method of treating a patient comprising rerouting blood flow from the pulmonary veins into a prosthetic chamber, and then back into a portion of the heart. The prosthetic chamber may include at least one valve, and may serve as a manifold for combining the flow of the pulmonary veins into a single return conduit, which may be placed into communication with the left ventrical.

Further features and advantages of the present invention will become apparent to those of skill in the heart in view of the detailed description of preferred embodiments which follows, when considered together with the attached drawings and claims.

DETAILED DESCRIPTION OF THE PREFERRED EMBODIMENT

Figure 1:
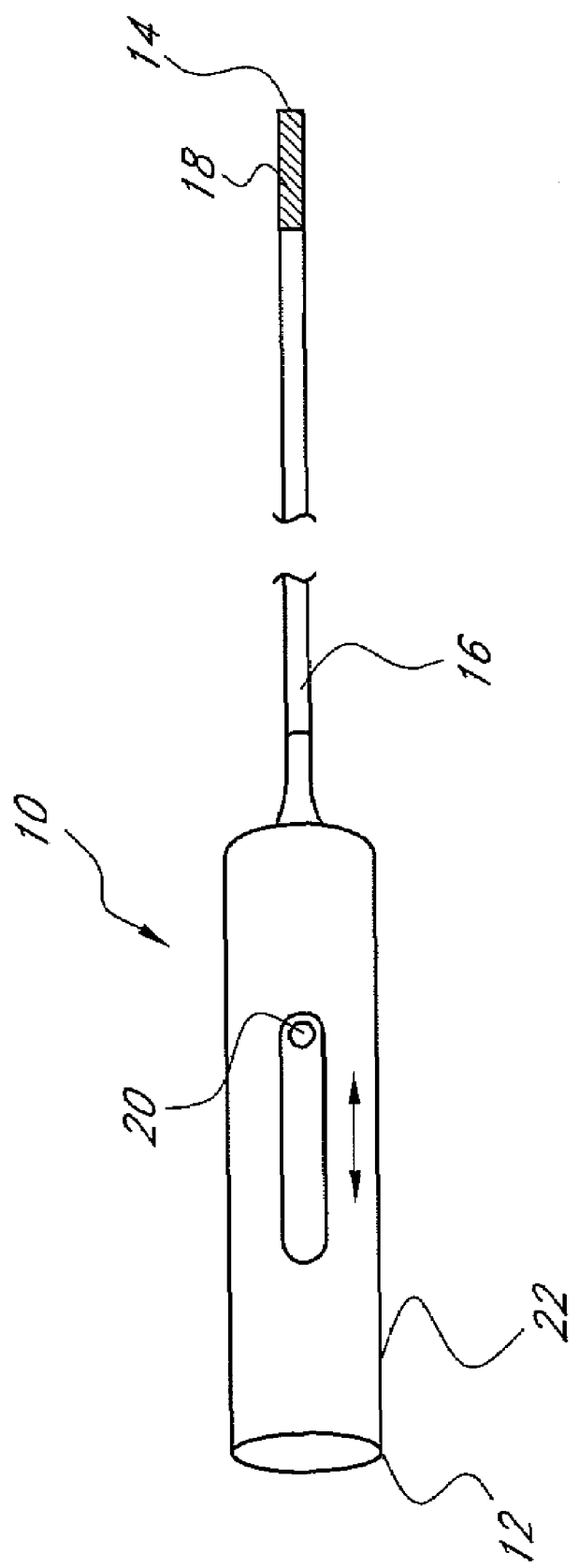
FIG. 1 is a side elevational schematic view of an axially actuated deployment device in accordance with the present invention.
Figure 2:
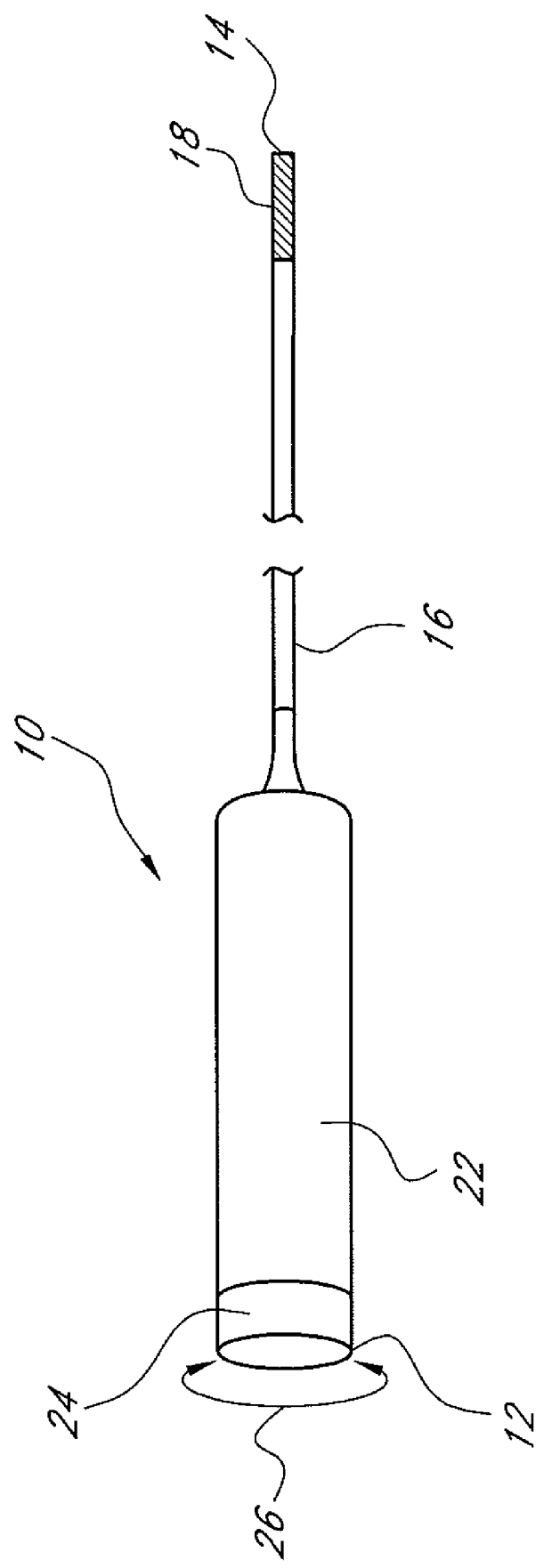
FIG. 2 is a side elevational schematic view of a rotationally actuated deployment device in accordance with the present invention.
Figure 3:
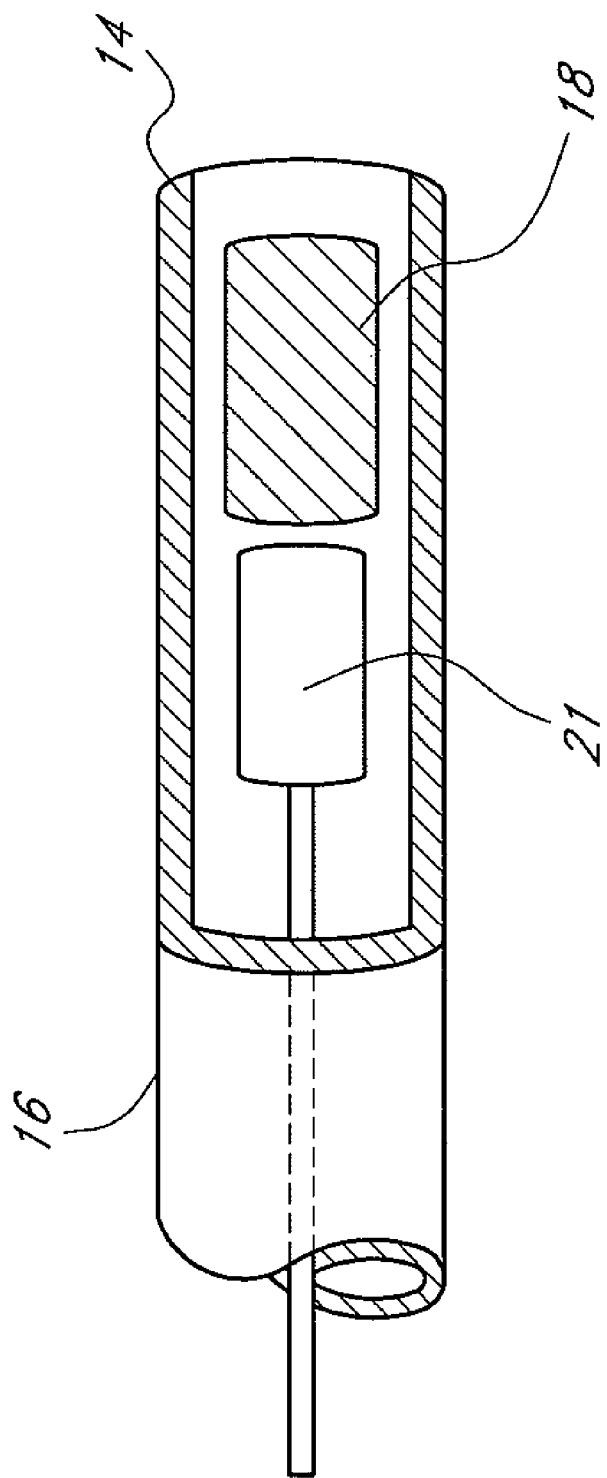
FIG. 3 is a fragmentary cut-away view of a distal end of a deployment catheter having an implantable device therein.
Figure 4:
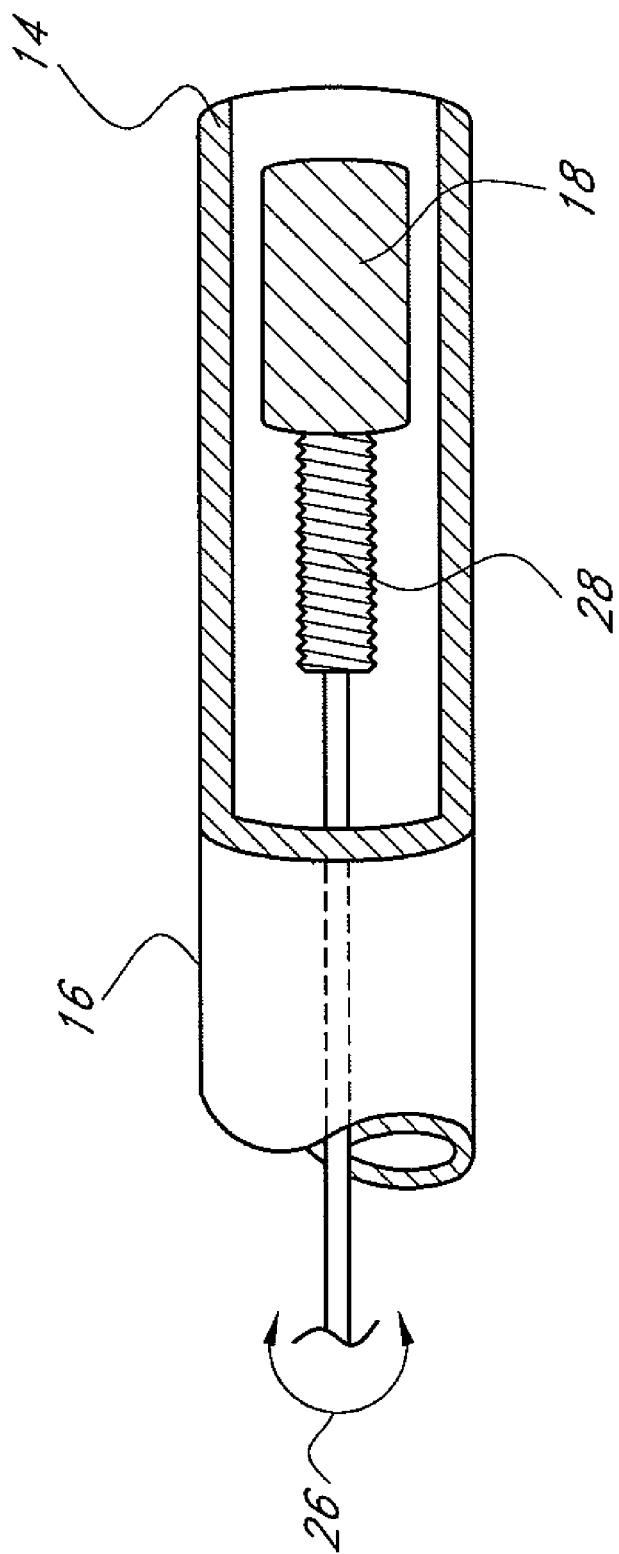
FIG. 4 is a fragmentary view as in FIG. 3, having a different embodiment illustrated therein.
Figure 5:
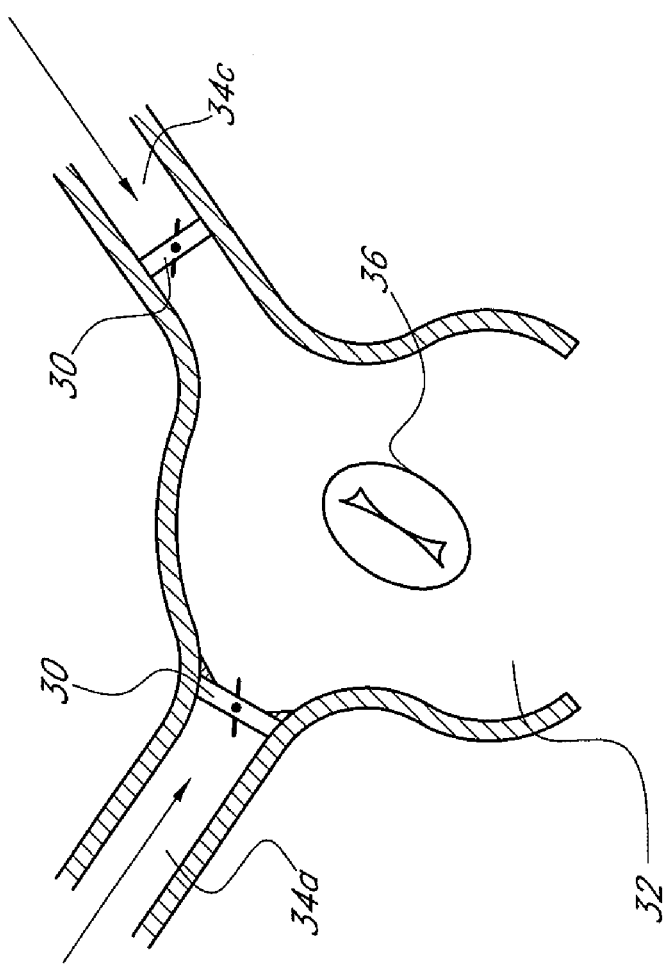
FIG. 5 is a simplified top view of a section through the heart, illustrating a first valve at a first location in a first pulmonary vein, and a second valve at a second location in a second pulmonary vein.

Implantation of valves into the body has been accomplished by a surgical procedure or via percutaneous method such as a catheterization or delivery mechanism utilizing the vasculature pathways. Surgical implantation of valves to replace or repair existing valves structures include the four major heart valves (tricuspid, pulmonary, mitral, aortic) and some venous valves in the lower extremities for the treatment of chronic venous insufficiency. Implantation includes the sewing of a new valve to the existing tissue structure for securement. Access to these sites generally include a thoracotomy or a sternotomy for the patient and include a great deal of recovery time. An open-heart procedure can include placing the patient on heart bypass to continue blood flow to vital organs such as the brain during the surgery. The bypass pump will continue to oxygenate and pump blood to the body's extremities while the heart is stopped and the valve is replaced. The valve may replace in whole or repair defects in the patient's current native valve. The device may be implanted in a conduit or other structure such as the heart proper or supporting tissue surrounding the heart. Vessels entering or departing the heart have an attachment or connection interface where the two components join in transition. This transition may provide a secure tissue zone to attach a valve body to. Attachments methods may include suturing, hooks or barbs, interference mechanical methods or an adhesion median between the implant and tissue. Access to the implantation site may require opening the wall of the heart to access the vessel or heart tissue for attachment. It is also possible to implant the device directly into the vessel by slitting in the longitudinal direction or cutting circumferentially the vessel and suturing the vessel closed after insertion. This would provide a less invasive method to implant the device surgically.

Other methods include a catheterization of the body to access the implantation site. Access may be achieved under fluoroscopy visualization and via catheterization of the internal jugular or femoral vein continuing through the vena cava to the right atrium and utilizing a transeptal puncture enter the left atrium. Once into the left atrium conventional and new catheterization tools will help gain access to the pulmonary veins. Engagement of each of the pulmonary veins may require a unique guiding catheter to direct device or catheter placement. Monitoring of hemodynamic changes will be crucial before, during and after placement of the device. Pressure and flow measurements may be recorded in the pulmonary veins and left atrium. Right atrial pressures may be monitored separately but are equally important. Separate catheters to measure these values may be required.

Valve delivery may be achieved by a pushable deployment of a self expanding or shaped memory material device, balloon expansion of a plastically deformable material, rotational actuation of a mechanical screw, pulling or pushing force to retract or expose the device to the deployment site. To aid in positioning the device, radiopaque markers may be placed on the catheter or device to indicate relative position to known landmarks. After deployment of the devices the hemodynamic monitoring will allow the interventional cardiologist to confirm the function of the valves. It is possible to place and remove each valve independently as valves may not be required in all pulmonary veins.

Entry to the body with a catheter may include the internal jugular or femoral vein. This will allow the user to enter the right atrium either superior or inferiorly and complete a transeptal puncture for access into the left atrium. Another approach would be to enter the femoral, brachial or radial artery where the user could access the aortic valve entering the left ventrical. Advancing the device through the left ventrical and past the mitral valve the left atrium can be entered. Utilizing normal cath-lab tools such as guidewires and guide catheters the delivery system or catheter can be advanced to the deployment site. Guidewires may measure 0.010-0.035 inches in diameter and 120-350 centimeters in length. Slippery coatings may aid in the navigation to the implantation site due to the vast number of turns and the tortuosity of the vasculature. A guide catheter may be used to provide a coaxial support system to advance the delivery catheter through. This guiding catheter may be about 60-180 cm in length and have an outer diameter of 0.040-0.250 inches. It would have a proximal and distal end with a connection hub at the proximal end and may have a radiopaque soft tip at the distal end. It may have a single or multilumen with a wall thickness of 0.005-0.050 inches and may include stiffening members or braid materials made from stainless steel, nickel-titanium or a polymeric strand. The catheter material may include extruded tubing with multiple durometer zones for transitions in stiffness and support. The inner diameter may have a Teflon lining for enhanced coaxial catheter movement by reducing the friction coefficient between the two materials.

As illustrated in FIG. 1, the delivery catheter 10 would be constructed by normal means in the industry utilizing extruded tubing, braiding for stiffening means and rotational torqueability. The delivery catheter 10 has a proximal end 12 and distal end 14 where the proximal end 12 may have a connection hub to mate other cath-lab tools to. The distal end 14 may have a radiopaque marker to locate under fluoroscopy. The outer diameter would measure about 0.030-0.200 inches and have a wall thickness from about 0.005-0.060 inches. The overall length would range from about 80-320 centimeters and have a connection hub or hubs at the proximal end 12 to allow wires, devices and fluid to pass. The connection hub would be compatible with normal cath-lab components and utilize a threaded end and a taper fit to maintain seal integrity. The inner diameter of the catheter 10 would allow for coaxial use to pass items such as guidewires, devices, contrast and other catheters. An inner lining material such as Teflon may be used to reduce friction and improve performance in tortuous curves. In addition a braided shaft of stainless steel or Nitinol imbedded into the catheter shaft 16 may improve the torqueability and aid in maintaining roundness of the catheter lumen.

Multidurometer materials would help soften the transition zones and add correct stiffness for pushability in the body. These zones may be achieved through an extrusion process know as bump tubing. Where the material inner and outer diameter change during the extrusion process. The entire catheter shaft can be produced in one piece. Another method for producing such a catheter shaft is to bond separate pieces of tubing together by melting the two components together and forming a single tube with multiple diameters and or stiffness. The application of heat can be applied by laser or heated air that flows over the shaft material or other methods of heat application sufficient to flow the materials together.

The shaft material may also consist of stiffening members for transition zones or bump extrusions to reduced diameter and maintain correct pushability. Lumen characteristics may include single or multi portals for guidewire or device entry. Conventional guidewire passage through the catheter such as "over-the-wire" may be used or technology such as "rapid-exchange" may aid in procedure ease and catheter exchanges. Since multiple devices may be placed in a single catheterization, rapid-exchange may be preferred but not essential. Other features that may aid in ease of use include a slippery coating on the outer and or inner diameter such as MDX (silicone) or a hydrophilic layer to allow easy access to tortuous anatomy. It may be necessary to utilize a balloon to radially expand the device to its final diameter and location so an inflation lumen and balloon placed distal to the hub could be used. This balloon could be used to pre-dilate the vessel or ostium where the valve may be implanted. Finally elements to transmit signals externally could be imbedded into the catheter for pressure and flow readings or Doppler information. These may include electrical wires, pressure portal or lumens optical fibers.

As illustrated in FIGS. 1-4, delivery of the device 18 via catheterization of the implantation site will include a mechanism to deploy or expel the device 18 into the vessel or atrium. This mechanism may include push or pull members 20 and 21 to transmit forces to the distal portion of the catheter 10. These forces may be applied externally to the body and utilize a handle 22 at the proximal end 12 of the catheter. Means to transmit forces to the distal end 14 may also include a rotational member 24 to loosen or tighten, convert a torque 26 into a translational force such as a threaded screw 28 and nut or to add or subtract stiffness to the catheter 10 or device 18. The handle 22 mechanism may also include a port for hydraulic pressures to be transmitted to the distal portion of the catheter 10 or have the ability to generate hydraulic forces directly with the handle 22. These forces may include a pushing or pulling transmitted to the device 18 or catheter 10, an exposure of the device 18 to allow for implantation or to expel the device 18 from the catheter. Further forces may include a radial or longitudinal expansion of the device 18 or catheter 10 to implant or size the location of implantation. The handle 22 may also include connections to electrical signals to monitor information such as pressures, flow rates, temperature and Doppler information. Another important use of the handle 22 and catheter 10 is the deployment mechanism for the device 18. As the device 18 is navigated to the site, attachment between the device 18 and catheter 10 is essential. Many detachment methods have been used to deploy devices 18 such as stents and embolic coils through balloon expansion and simple pushable coils expelled from the distal end 14 of a catheter 10. The valve device can utilize many different methods to implant at the selected site such as an expulsion out the end of the catheter 10, a mechanical release mechanism such as a pin joint, unscrewing the device 18 from the catheter delivery system, a tethered link such as a thread or wire, a fusible link as used in a GDC coil deployment, a cutting tool to sever a attachment of the device 18 from the catheter 10, a threaded knot to tether the catheter 10 to the device 18 where the as the knot could be untied or cut, a hydraulic mechanism to deploy, expand or fracture a link between the catheter 10 and the device 18. All above mentioned concepts may be enhanced be the utilization of a flexible tip to allow acute articulation of the device 18 and delivery catheter 10 to gain access to the implantation site.

After the device has been temporarily deployed or positioned, it may be advantageous to recapture or reposition the device for optimal results. This may include a rotational or translation of the implant of a complete removal and exchange for a different diameter, length or style device. Capture of an implanted device may require a second catheter to reengage the device to remove or reposition to a proper location.

Valve

As illustrated in FIGS. 5-8, in the preferred embodiment the device, such as a valve 30, would be located between the right lung 31a and/or left lung 31b and the left atrium 32 in the right superior pulmonary vein 34a, the right inferior pulmonary vein 34b, the left superior pulmonary vein 34c, the left inferior pulmonary vein 34d and/or in the wall of the left atrium 32. Preferably the valve 30 described above is located to affect the flow and pressure of blood between the pulmonary veins 34a-d and the left atrium 32 or a portion of the left atrium 32 and to lessen the symptoms of mitral regurgitation from a dysfunctional mitral valve 36 including elevations and fluctuations in the pulmonary circulation. The device 30 may be viewed as a one-way valve limiting or restricting retrograde flow into the pulmonary circulation. Having a substantial fatigue life to withstand cyclical operation for a given period of implantation duration will be a factor in selection of both materials and construction. This may include heat treatments to certain portions or all components of the device 30 and analysis of construction and manufacturing techniques to optimize device 30 life. Additionally a coating may be required to maintain patency of the device 30 during normal operation. This may be a surface modification or treatment, a coating added to the device 30 such as heparin or and albumin layer.

The valve could be a valve of any design including bioprosthetic, mechanical or tissue valves. Examples of commonly used prosthetic valves include a ball valve 40 illustrated in FIG. 9A such as a Starr-Edwards, a single leaflet valve 50 illustrated in FIG. 9B such as a Bjork-Shiley valve, a bileaflet or bi-disk valve 60 illustrated in FIG. 9C or an artificial tricuspid valve such as a Magna or Cribier, a reed style valve 70 illustrated in FIG. 9D, a slit in a membrane of material, a duckbill style or many other styles unmentioned here but apparent to one skilled in the art. To facilitate delivery of the valve and to improve hemodynamics other mechanical valve designs may be utilized, including the poly-leaflet valve and flexible leaflet valves as described below. The valves may be deformable to allow for percutaneous delivery or rigid to enable structural integrity. They may include one of the below mentioned features or a combination of a plurality thereof to add performance and or reduce size.

Mechanical

Figure 9A:
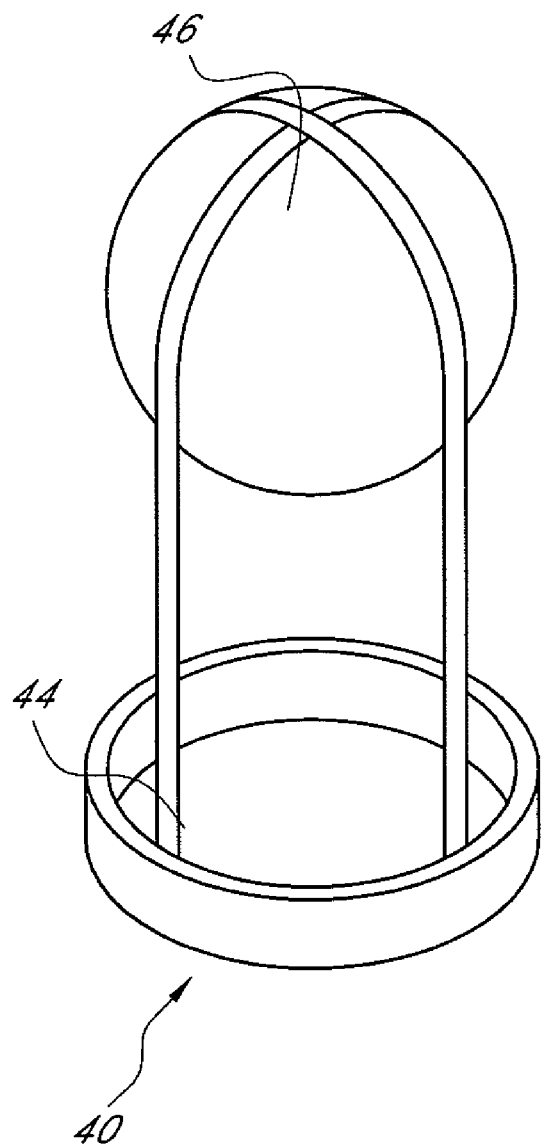
FIG. 9A is a perspective schematic view of a Starr-Edwards ball and cage valve.

As illustrated in FIG. 9A, the early valve implants began in the early 1960's with ball valves 40 such as the Starr-Edwards. This valve 40 includes a base 42 and mechanical structure 44 where a ball 46 is captured and allowed to travel longitudinally sealing flow in one direction and allowing flow in the other. The movement of the ball 46 is driven by flow.

Figure 9B:
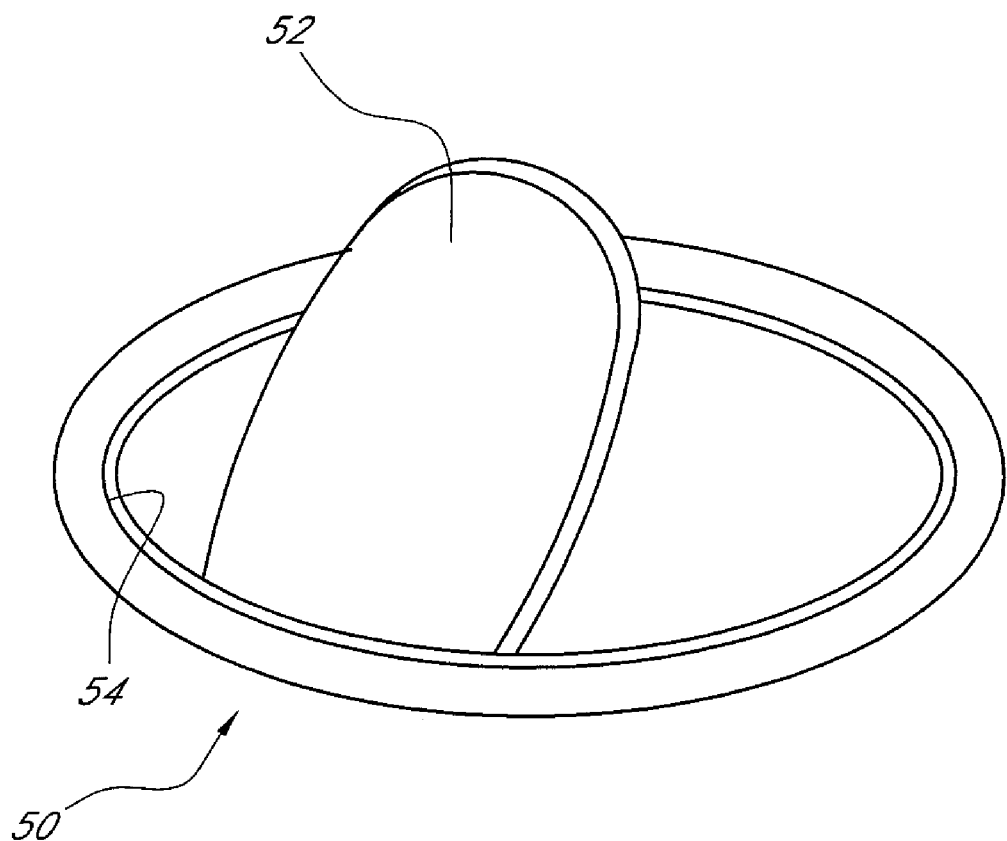
FIG. 9B is a perspective schematic view of a single leaflet valve.

As illustrated in FIG. 9B, disk style valves 50, known as Bjork-Shiley, entered the market in the 1970's and began with a single disk 52 supported in a ring 54 where the disk 52 was allowed to pivot within the ring 54 allowing flow in one direction and sealing flow in the other. The tilt angle ranged from about 60-80 degrees.

Figure 9C:
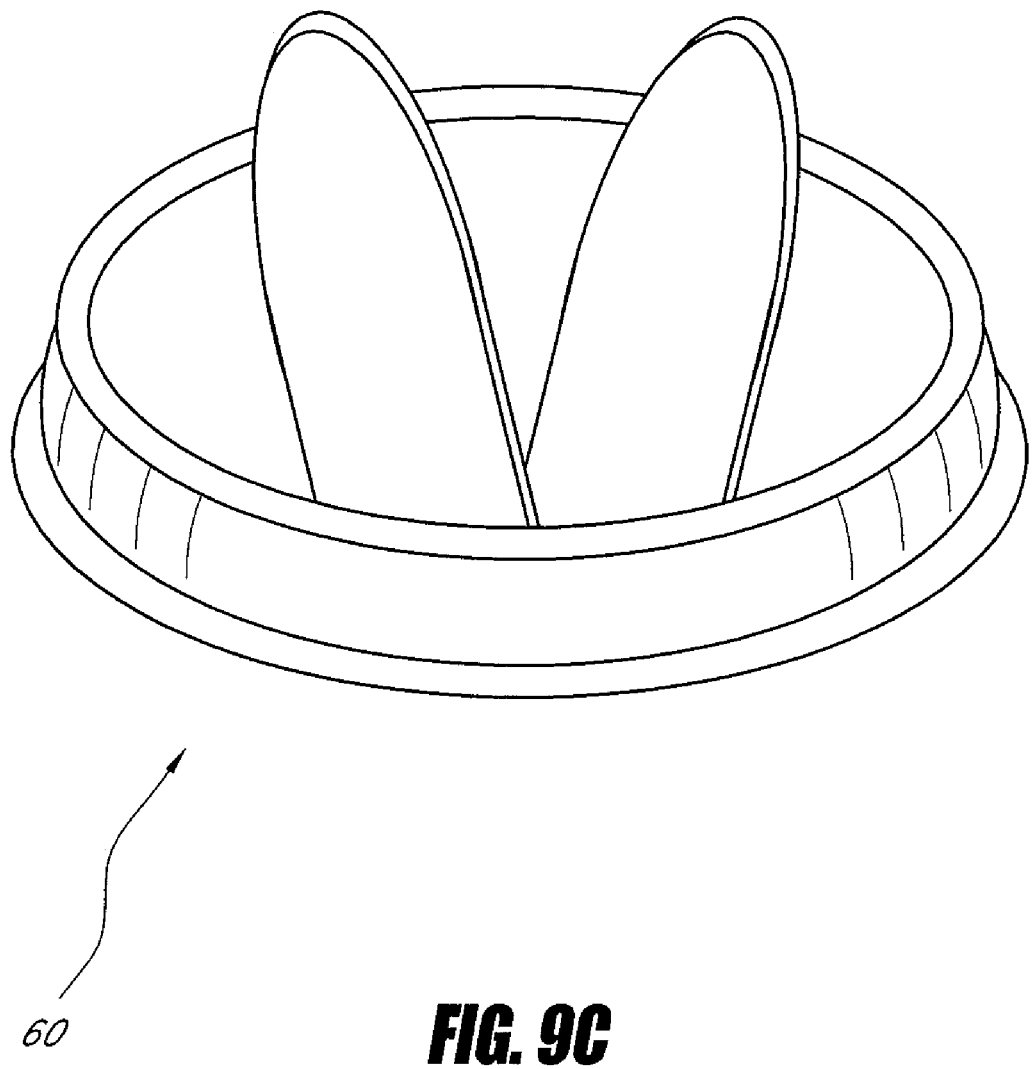
FIG. 9C is a schematic perspective view of a bi-leaflet valve.
Figure 9D:
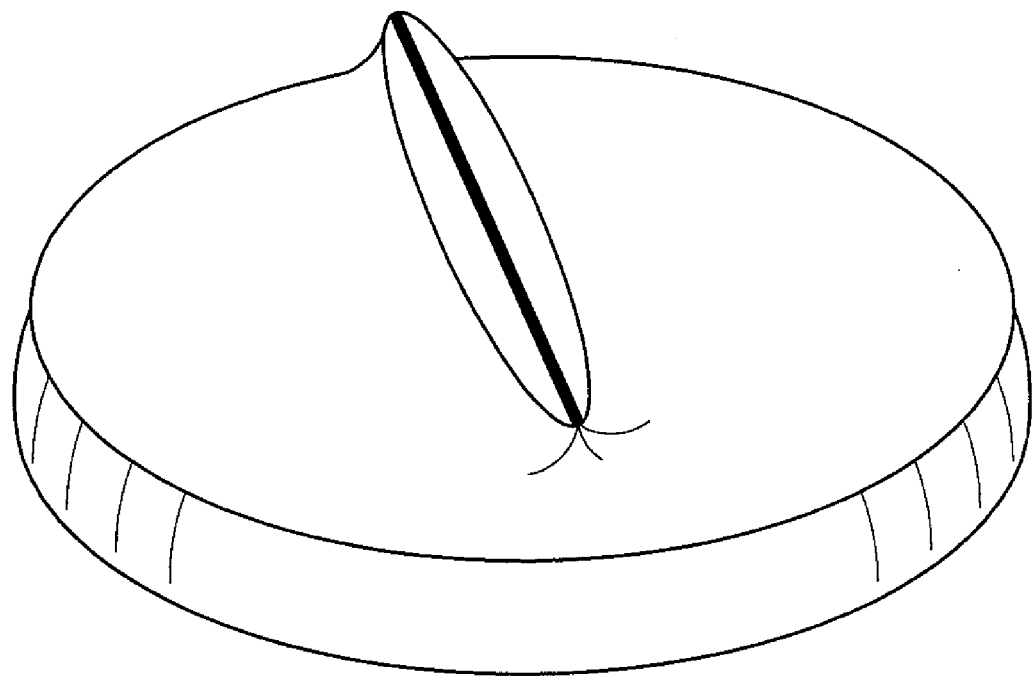
FIG. 9D is a schematic perspective view of a Reed style or duckbill valve.
Figure 9D:
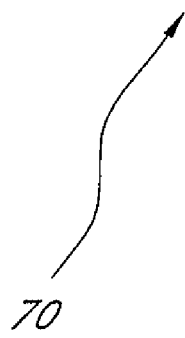

As illustrated in FIG. 9C, bi-disk valves 60 include two tilting disks to allow for greater flow and less turbulence. These valves 60 were introduced in the 1980's and seem to be the standard choice.

Figure 9E:
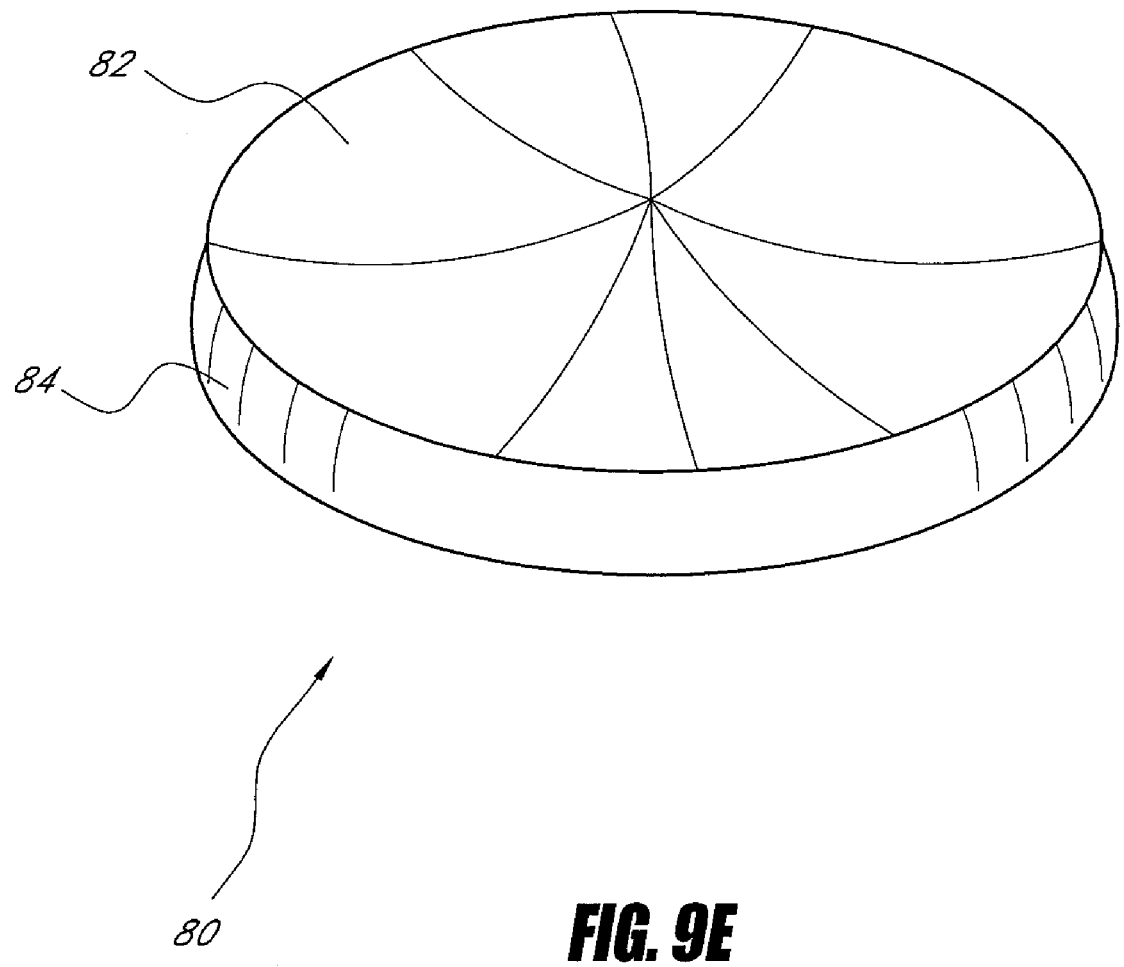
FIG. 9E is a schematic perspective view of a poly-leaflet valve.

As illustrated in FIG. 9E, also disclosed is a poly-leaflet valve 80 for implantation in the body. The valve 80 would contain four or more leaflets 82 free to pivot near the annulus 84 of the valve 80. Increasing the number of leaflets 82 allows the valve 80 to collapse to a smaller diameter, for percutaneous or minimally invasive delivery, while also providing good hemodynamics, and allowing the leaflets 82 to be made from a rigid material ideally one that has clinically proven good biocompatibility in valve applications.

Also disclosed is a flexible leaflet valve for implantation in the body. A mechanical prosthetic valve manufactured from a flexible material such as a polymer or tissue material that allows the leaflets to be substantially deformed during delivery if the valve. The leaflets could also consist of metal or a polymeric coated sub straight. If metallic the leaflet material could be a super elastic alloy such as Nitinol or an alloy with a relatively high yield stress and relatively low modulus of elasticity such as certain titanium alloys. Someone skilled in the art will understand the relationship between elastic modulus and yield stress; in order to select materials with a maximum amount of strain available before yielding begins. This would allow for recoverable deformation during delivery and may enhance fatigue characteristics.

A valve that functions as an iris could also be utilized as a prosthetic valve. The iris could be opened and closed by an internal or external force, a differential in pressure or by the flow of blood.

Tissue

There are several types of tissue valves that have been previously implanted as replacement valves in the human coronary system. These include valves from human cadavers, and valves from other mammals such as pigs horses and cows utilizing sometimes pericardial tissue to build a valve by sewing techniques. Any of these types of valves could be implanted as described both in a surgical procedure or a catheterization. Additionally other valves such as from the larger venous vessels from smaller animals could be utilized because of the smaller size and reduced flow requirements of the pulmonary veins.

A valve from the patient may also be used, by transplanting the valve into a pulmonary vein. Many native valves could be used such as a venous valve from the lower extremities. The preferred embodiment is to use a native valve from a large peripheral vein.

Orifice

The flow control device could be an orifice of fixed or adjustable diameter that limits the amount of blood that flows through the pulmonary veins. The orifice diameter could be adjusted remotely or by some hemodynamic mechanism such as pressure or flow differential or pressure change.

Flap

The flow control device could consist of one or more flaps located within the atrium to prevent the back flow of blood into the pulmonary veins. The flow control device could be a pivoting or flexible flap that moves to block the ostium of one or more pulmonary veins or it could be a rigid or semi rigid flap or flaps that control the bloods flow path reducing or eliminating the backwards flow of blood in to the pulmonary veins.

Flow Controlled

In the preferred embodiment the flow through the valve is flow controlled. To the extent possible flow is allowed only in a first direction and not in a second direction. The first direction is intended to be away from the lungs and towards the heart.

Pressure Controlled

The valve may function such that it is pressure controlled that is it opens at a preset pressure differential. The pressure control could be implemented in several ways. The one-way valve could allow flow in the backward or restricted direction at a certain pressure differential. This may be advantageous in preventing the overloading of the atrium. Alternatively the valve could be designed to open in its normal flow direction at a preset pressure differential.

Metallic

The valve or flow control device may be manufactured partially or completely from metallic components. Depending on the mechanical properties required various biocompatible metals might be chosen. These include, but are not limited to various stainless steel alloys, cobalt-chrome-nickel-alloys, super-elastic alloys such as Nitinol, Tantalum and titanium and its alloys. The device could be self-expanding in nature if desired.

Polymer

The valve or flow control device may be manufactured partially or completely from polymeric components. Various biocompatible polymers may be used depending on the desired mechanical properties. Some examples of biocompatible polymers include silicone, polyethylene and, fluoropolymers such as Teflon.

External Cuff

All or part of the flow control device may attach to the outside of the pulmonary vein by applying external force to the vein the device affects the flow through the vein. Both compressive or expansive forces could be applied to change the vessel geometry. An external portion of the device located around the vein may also help to secure a second portion of the device within the vein.

Electrical

Valves may be actuated to synchronize with the proper opening and closing times through an internal or external device such as a pacemaker. There may require an actuation device to drive the motion of the valve open and closed. Pressure gradients could be used to sense when actuation is necessary.

Vane

The flow control device may include a vane that introduces a swirling motion to the blood. The vane may be used to improve hemodynamic flow through another portion of the flow control device or it may be used alone to improve the hemodynamics of the native anatomy. The vane may additionally function or rotate in a single direction only to limit flow.

Pump

In one embodiment the flow control device located between a portion of the pulmonary veins and the heart consists of a pump. The pump may be powered externally, internally or by the biological movement of the heart. The pump may be located inside the pulmonary vein inside the atrium outside the heart or, outside the body.

Inflatable Support Structure

As illustrated in FIGS. 9F, 9G, 9H and 11, certain pulmonary vein valves in accordance with the present invention include an inflatable support structure 90, as is disclosed, for example, in the context of an atrial valve, in the provisional applications incorporated by reference above.

Figure 9F:
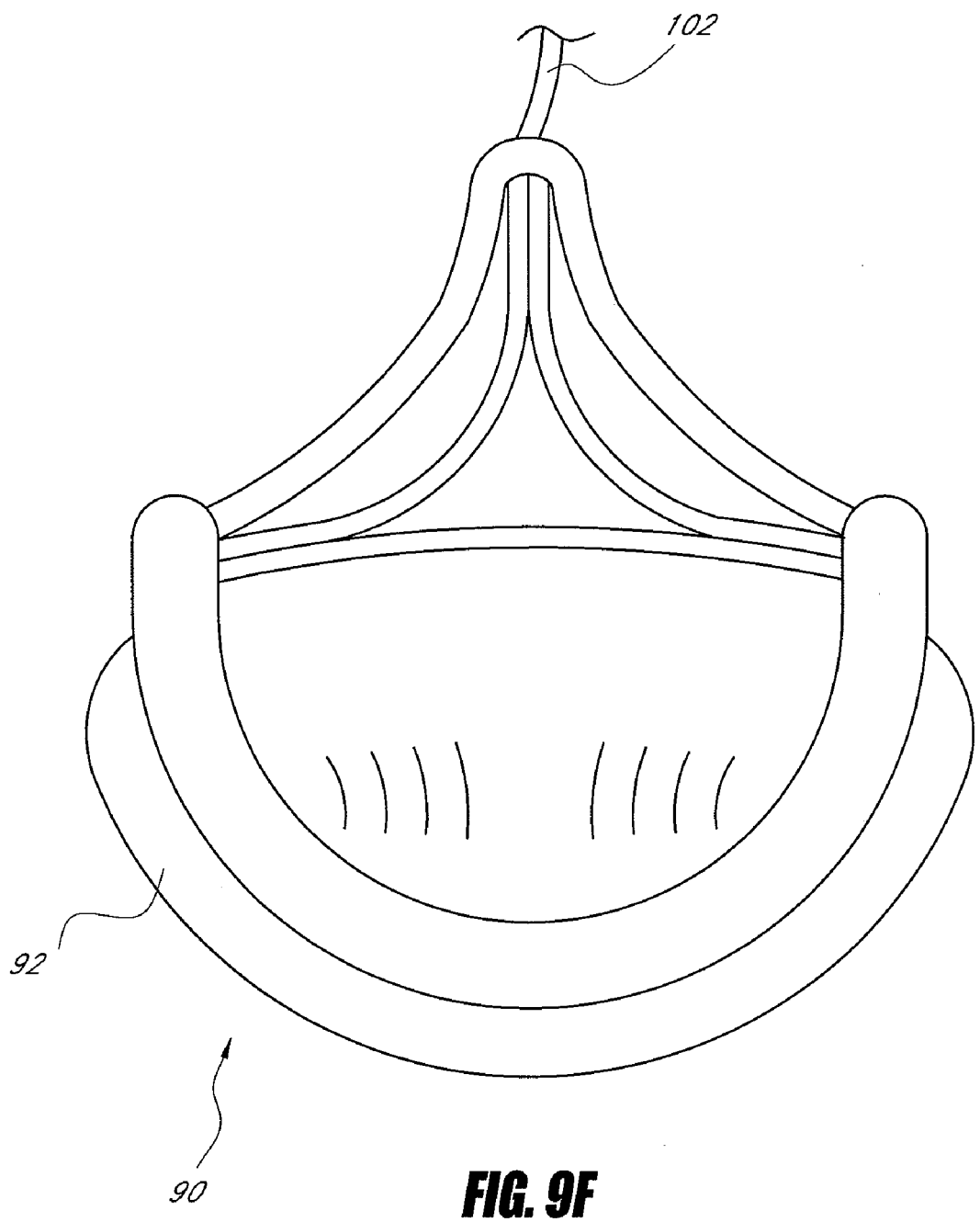
FIG. 9F is a schematic perspective view of a tri-leaflet valve having an inflatable support structure.
Figure 11:
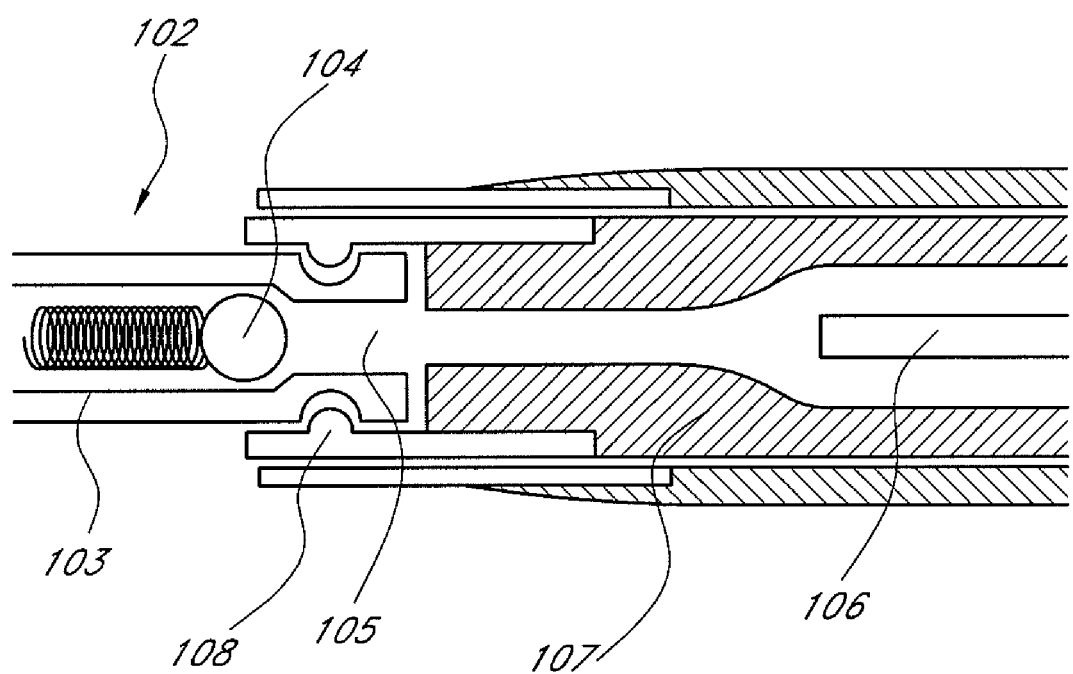
FIG. 11 is a cross-sectional view of a ball valve that can be used to control inflation of the inflatable support structure.

As illustrated in FIGS. 9F and 11, the inflatable support structure 90 comprises at least one annular ring 92, such as an annulus for a valve, which is releasably carried by a deployment catheter having at least one inflation lumen extending therethrough. Following positioning of the valve in the pulmonary vein, the annulus is inflated to the desired size and/or pressure, and thereafter decoupled from the deployment catheter. A one wayvalve 102 on the inflatable support structure 90 prevents escape of the inflation media and/or allows inflation of the inflatable support structure 90. The one way valve 102 can be a ball valve, as illustrated in FIG. 11, or another type of valve such as a duck bill valve, pinch or flap valve. The flow control valve 102 illustrated in FIG. 11 has a spring 103 actuated check ball 104 that seals off the inflation lumen 105. A push wire 106 in the delivery catheter 107 can be used to displace the check ball 104 from the default sealing position, thereby unsealing the inflation lumen 105 and permitting the inflatable support structure 90 to be inflated. Release tangs 108 can be used to secure and align the delivery catheter 107 with the flow control valve 102.

Figure 9G:
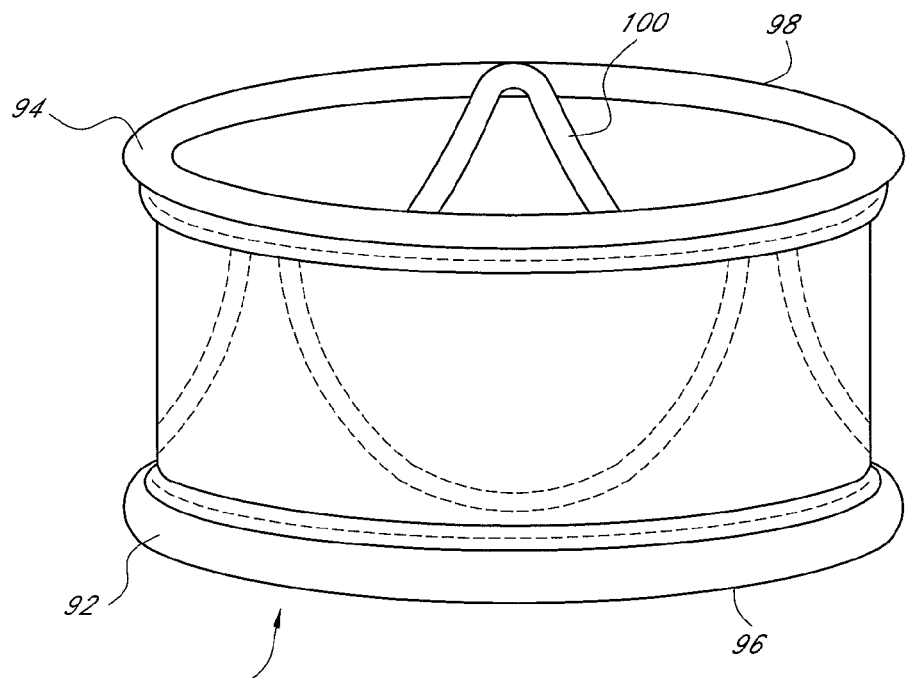
FIG. 9G is a schematic perspective view of a tri-leaflet valve having an alternative inflatable support structure.
Figure 9H:
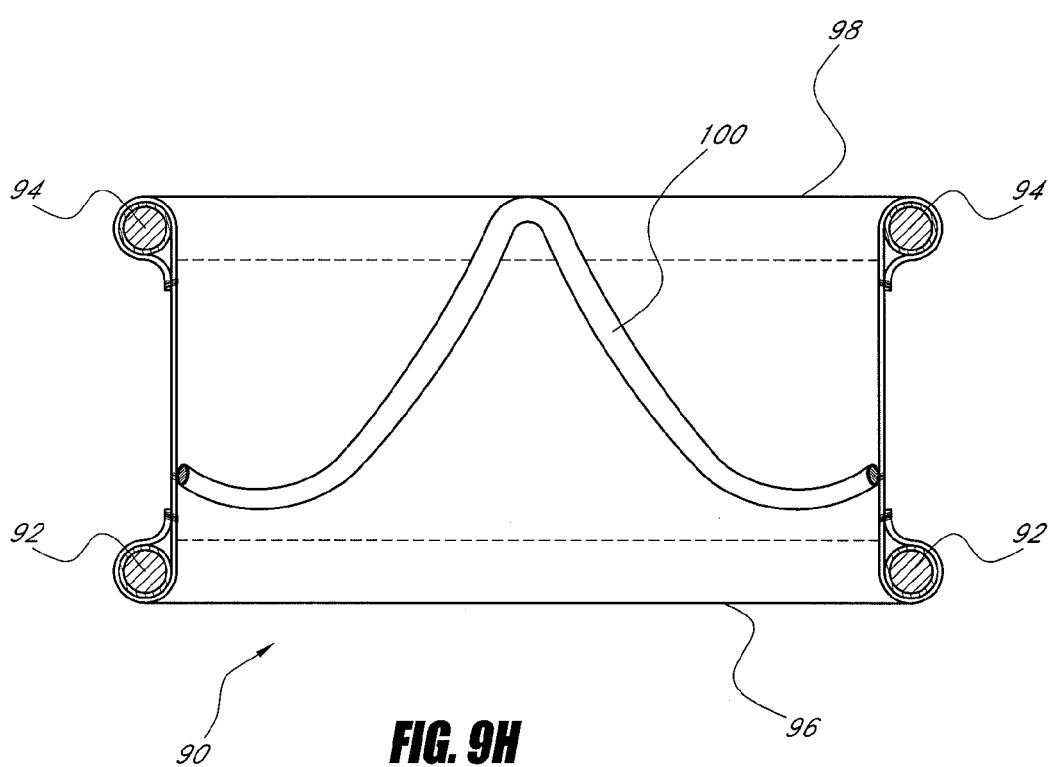
FIG. 9H is an elevational cross-sectional view through the valve of FIG. 9G.

As illustrated in FIGS. 9G and 9H, in certain embodiments, the first inflatable chamber 92 is provided such as at the annulus of the valve 90, and at least a second inflatable chamber 94 is provided, such as to provide commissural support and/or to stabilize the valve 90, depending upon the occluder (i.e. leaflet) configuration as will be appreciated by those of skill in the art in view of the disclosure herein. In one embodiment, a first inflatable ring 92 is provided at a proximal end 96 of the tubular valve 90, a second inflatable ring 94 is provided at a distal end 98 of the tubular valve 90, and at least one additional inflatable chamber 100 is provided in between the proximal and distal ends 96 and 98, to provide intermediate support. The intermediate support chamber 100 may comprise any of a variety of configurations, such as a zig-zag configuration around the circumference of the valve support structure. A tissue valve or a synthetic leaflet valve may be secured within the tubular valve support structure 90.

Prosthetic Atrium

Figure 10:
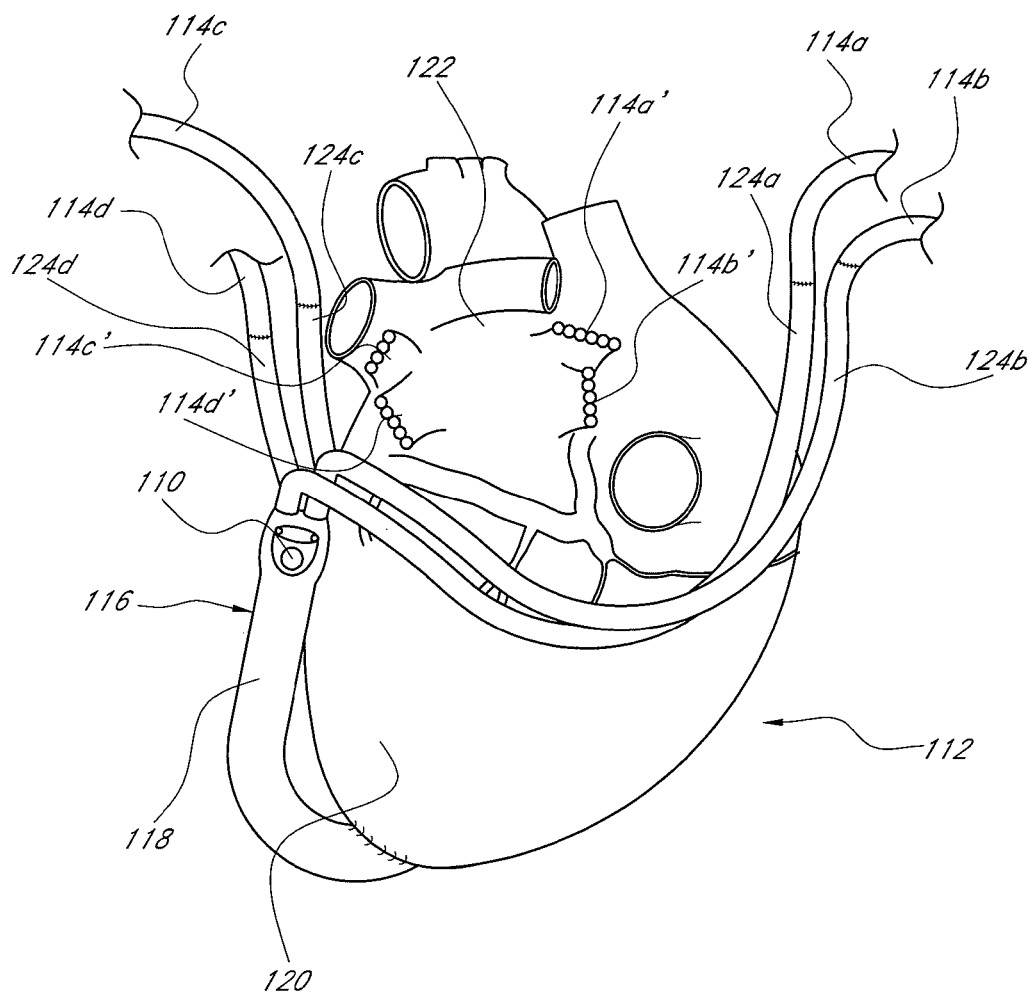
FIG. 10 is a schematic representation of the heart and pulmonary venous circulation following redirection of the pulmonary venous flow into the left ventrical.

As illustrated in FIG. 10, in one embodiment the device 110, such as a valve, is located substantially outside the heart 112. The right superior pulmonary vein 114*a*, the right inferior pulmonary vein 114*b*, the left superior pulmonary vein 114*c* and the left inferior pulmonary vein 114*d* are spliced into and connect together into a prosthetic atrium 116. Blood is then directed through a one-way valve 110 and through a conduit 118 to the left ventricle 120. The native mitral valve could be surgically sealed off and/or the native pulmonary veins 114*a*'-*d*' could be sealed, restricted, occluded, or cut, near where they connect to the left atrium 122. This procedure could be performed in an open surgical procedure or in a minimally invasive procedure or percutaneously, ideally the procedure would be performed on a beating heart possibly using a thorascope.

In the preferred embodiment where the procedure is performed on a beating heart 122, the prosthesis 116 is first flushed and filled with a biocompatible fluid such as saline to prevent the possibility of an air embolism. Next the outlet conduit 118 is attached to a portion of the native anatomy, preferably the left ventricle 120, and preferably near the apex of the heart 112. The one way valve 110 portion of the implant prevents blood from the left ventricle 120 from escaping uncontrolled. As a next step a pulmonary vein 114*a*-*d* is cut. The atrium 122 side of the vein 114*a*'-*d*' is tied off or otherwise sealed. The section of the pulmonary vein 114*a*-*d* connected to the lungs is attached to one of the inlet conduits 124*a*-*d* of the prosthesis 116. In a similar fashion the remaining pulmonary veins 114*a*-*d* are connected to the prosthesis 116, preferably one at a time.

In one embodiment the prosthetic atrium is supplied as a chamber with single outlet conduit 118 and four inlet conduits 124*a*-*d*. A one way valve 110 is supplied, attached either to the chamber or in the outlet conduit 118. Alternatively the outlet conduit 118 may be designed to allow the insertion and attachment of an available prosthetic valve 110 during the procedure. In one embodiment the prosthetic chamber is constructed from a woven fabric, such as polyester. In another embodiment the chamber is constructed from animal tissue such as the aortic root of a pig or the pericardial tissue from a cow. These tissues may be fixed using techniques common in the industry, such as glutaraldehyde fixation.

In a similar embodiment the blood is directed from the pulmonary veins, into the prosthetic atrium, past the prosthetic valve and then into the native atrium.

The prosthetic atrium could be of any volume, from as small as is practical to larger than a native atrium. The compliance of the prosthetic atrium is also a variable that may be adjusted to achieve optimal hemodynamics and to limit pulmonary edema.

In another embodiment the pulmonary veins are interrupted and blood is channeled from the portion of the pulmonary vein nearest the lung, through a prosthetic valve and then back into the portion of the pulmonary vein nearest the atrium. A valve could be placed in one or more pulmonary vein. Alternatively multiple veins could be joined to channel blood to a single valve. The flow of blood could then return to the heart in a single conduit or could be bifurcated into multiple channels and return to the heart, ideally through the ostium where the native pulmonary veins met or meet the atrium.

In yet another embodiment the valve is located substantially within the pulmonary veins or the atrium, but the valve is inserted through a slit cut into the pulmonary veins. It is possible that by interrupting flow in less than four of the pulmonary veins and or by a rapid surgical procedure, the use of a heart lung machine would not be required to oxygenate the patients blood.

Location

Location between the lungs and left atrium within the pulmonary veins will allow for single direction flow and protect the lungs from unwanted elevation in pulmonary pressures and fluctuation. The device could be implanted at any location within the pulmonary vein and may allow additional compliance if implanted deep into the pulmonary vein. This may allow the vein to dilate during higher pressures relieving pressures seen in the left atrium or pulmonary circulation. Additionally, an accumulation or expansion chamber may added to the pulmonary vasculature to allow for pressure variations. This device could be adjusted or calibrated to the correct or ideal pressures as normally seen in a healthy human and translate them to the pulmonary circulation. Another device may be located in the left atrium and consist of a bladder containing a fluid such as a gas to relieve excess pressures seen within the left atrium.

In one embodiment the device is located in the pulmonary veins near or at the ostium where the veins empty into the left atrium. The valves could be placed in this location by many methods including surgically or percutaneously delivery.

In another embodiment the device is located further up the pulmonary veins closer to the lungs. This location could effectively produce a more compliant and larger volume atrium than the previous embodiment.

In another embodiment the valve is located substantially within the atrium. With this valve location it may be possible to fit a larger valve for improved hemodynamics, or to allow the valve to cover the flow from more than one pulmonary vein. This may also aid in anchoring the device securely.

Anchoring Methods

Figure 6:
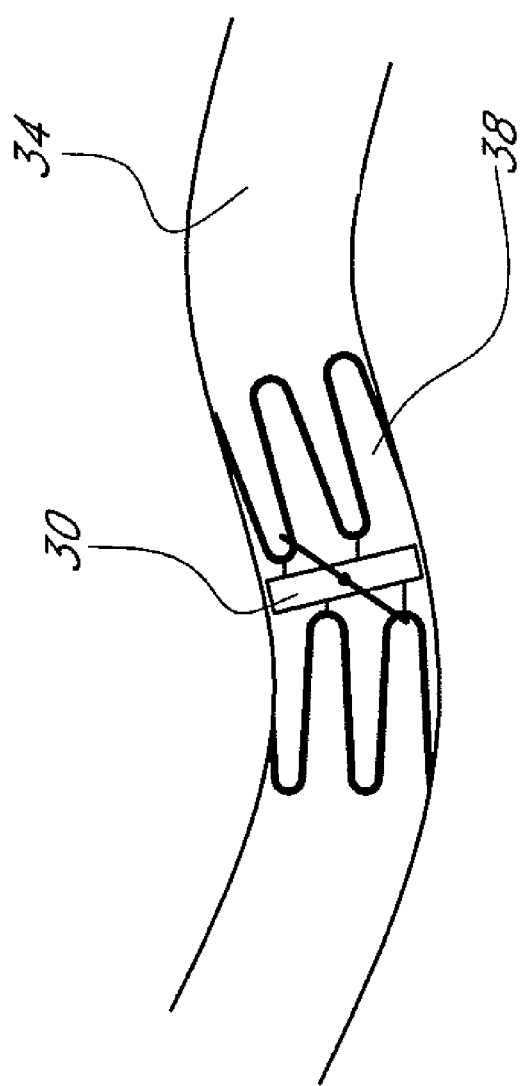
FIG. 6 is a schematic representation of a stent supported valve in a pulmonary vein.
Figure 7:
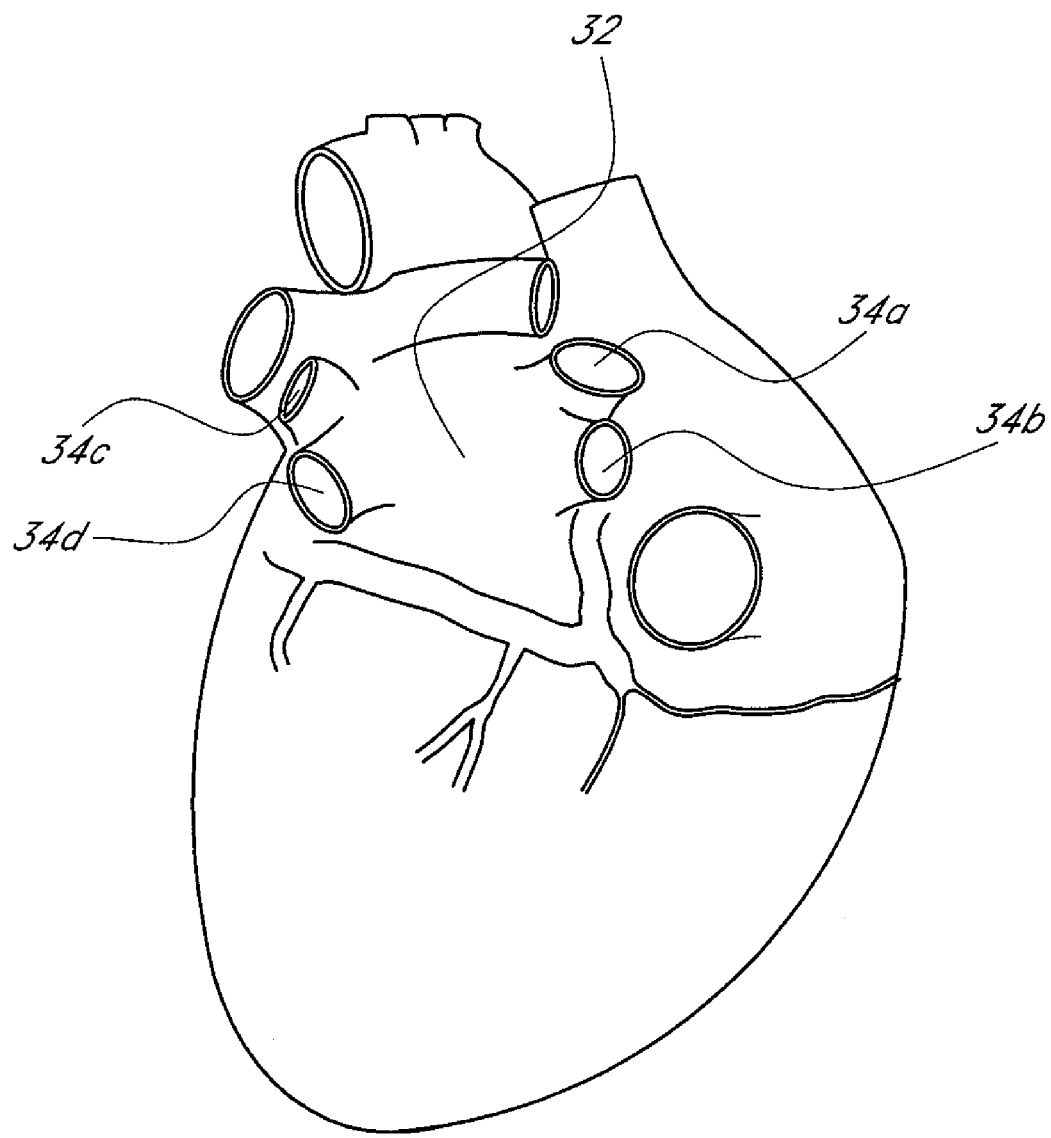
FIG. 7 is a simplified back view of the heart, illustrating the location of the left superior pulmonary vein, left inferior pulmonary vein, right superior pulmonary vein and right inferior pulmonary vein.
Figure 8:
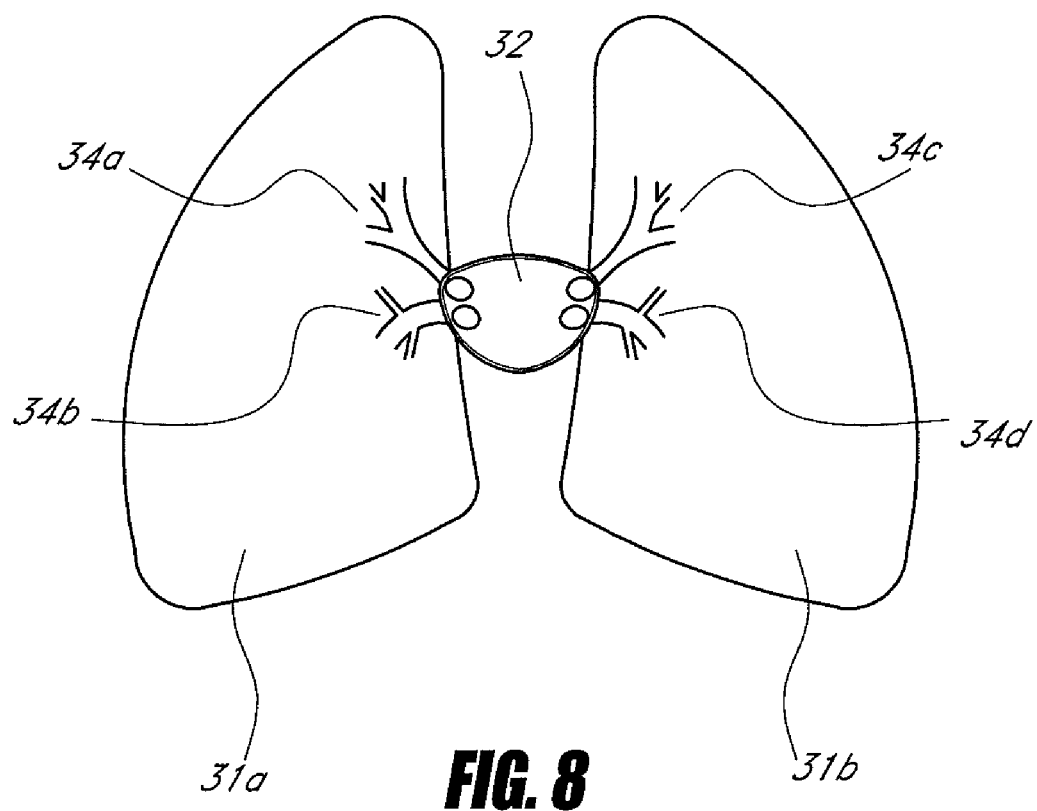
FIG. 8 is a simplified view of the lungs and left atrium, illustrating the orientation of the pulmonary veins with respect to the lungs.

The flow control device can be secured in the anatomy by several methods. As illustrated in FIG. 6, in one embodiment a portion of the device 30 consists of an expandable stent like structure 38 utilizing an interference fit or surface friction to hold the device 30 in place. The stent like structure 38 could be made from a malleable alloy such as a stainless steel of suitable alloy and condition or cobalt-chromium for better visibility under fluoroscopy. The stent like structure 38 would then be expanded mechanically by a balloon or other means, producing interference fit with the tissue. Alternatively the stent like structure 38 could be one of a self-expanding design, manufactured from a super elastic material such as Nitinol, or a material with a large amount of elastic strain available such as the ellgilloy used in the wall stent. The stent 38 could be manufactured from a tube selectively removing portions with a laser or EDM thus providing optimal expansion and cross-sectional profiles. One skilled in the art of stent design and manufacture could produce many variations of an embodiment as such.

Another anchoring method is to suture the valve portion to the wall of the atrium or to the pulmonary vein. The flow control device may contain a sewing ring to allow sutures to be easily attached to the device. A percutaneous or minimally invasive sewing device may also be incorporated. This device would contain at least one needle remotely actuated to attach the valve to the tissue, or to a second device previously implanted at the desired valve location. Other methods may utilize a balloon or other force mechanism to push or pull the suture into position.

Another anchoring method is to staple or clip the valve in place with multiple detachable staples, clips, barbs or hooks. This could be accomplished surgically with a tool that spaces the clips around the annulus and allows them to engage the tissue and a portion of the valve. The staples, clips, hooks or barbs could also be delivered percutaneously with a device that positions the staples, clips, hooks or barbs relative to the valve. These could be attached through a balloon or other force mechanism to push or pull them into position.

Another anchoring method is to use an adhesive to secure the valve to the tissue. Adhesives such as a fibrin glue or cyanoacrylate could be delivered percutaneously or surgically to attach the valve to the tissue.

Size Range

The devices could be made in a variety of diameters to correspond to the various anatomy of the patient population. The ideal size of the flow control device designed to be located inside a pulmonary vein may not directly correspond to the diameter of the vein. For example in some cases an oversize valve may be preferred because it may offer better hemodynamics or other advantages. In other cases an undersize valve may be preferred because it may offer reduced vessel trauma or other advantages. The average size of the pulmonary veins is approximately 15 mm in diameter. These valves would preferably be manufactured in a range of sizes from 3 to 30 mm in diameter, although other sizes may be used.

A flow control device designed for location in the atrium may have a range of sizes significantly larger than the previous embodiment these valves may preferably range from 8 to 80 mm in diameter, although other sizes may also be used.

A flow control device designed to be located substantially outside the heart and outside the pulmonary veins may include a valve of a range of diameters from 8 to 80 mm.

An orifice type flow control device if located in the pulmonary vein would require an outside diameter corresponding to the diameter of the vein. The inside diameter would depend on the desired effect on flow. The outside diameter would preferably be approximately 10-20 mm in diameter and may range from 3 to 30 mm in diameter. Other sizes may also be used. The internal diameter of the orifice may range from 1 to 20 mm in diameter. An orifice designed to limit flow through the native arteries when a secondary path for blood flow is provided may be smaller still. In this case an orifice from 0.5 to 5 mm is preferred, although other sizes may be used.

Length of device may vary depending upon the style selected. Disk style devices may range in length from 2-20 millimeters where a ball-cage style may range from 2-30 millimeters in length. It is also possible to implant a plurality or devices into one vessel for additional performance. The valve portion of the implant may be located distal, proximal or coaxial to the anchoring portion of the device. The anchoring portion of the device may range in length from 2-30 millimeters.

Congenital Defects

Devices of similar or identical design could be used to treat patients with congenital defects. For example a patient with a common atrium, where the septal wall between the left and right atrium is missing could be treated with a device described above, although the patient does not have a left atrium the common atrium serves its function and a similar device could be effective. In another example a patient suffering from a transposition of the great cardiac veins could be treated with a similar valve.

Procedure

Cath-Lab

The procedure is preferably performed in a cardiac catheterization lab, where the normal tools associated with interventional cardiology are available. Many of the conventional tools could be used for the implantation of a valve controlling the flow through the pulmonary veins. These tools include items such as introducers guide catheters, and guide wires may be used with this device. Some devices specifically designed for the valve implantation such as special sizing tools to measure diameters and flow characteristics and access tools to engage the pulmonary veins may be used. A guide catheter with a special curve or curves may be required to access the atrium and pulmonary veins. The device is to be implanted using fluoroscopic guidance or other visualization means such as CT or MRI. A contrast media such as barium sulfate may be used to visualize the coronary anatomy. Contrast could be injected into the pulmonary artery, or one of its branches, to help visualize where the pulmonary veins exit the lungs. Contrast could also be injected from the tip of the guide catheter when engaged into the pulmonary vein to image the ostium clearly for device placement.

Surgical Suite

Another method of implanting the valve between the pulmonary veins and the heart is a surgical approach. This procedure is to be performed in a surgical suite. The heart may be exposed by a sternotomy or lateral thoracotomy or through a portal entry or the procedure is performed through a puncture or small incision utilizing a minimally invasive tube like device.

In one version of the procedure the aorta is cross-clamped and the heart is infused with a cardiopelegic solution. A bypass pump is utilized to provide oxygenated blood to the body especially important organs such as the brain.

In another version surgical tools are utilized to allow the procedure to be performed through small incisions in the heart, preventing the need for the use of the bypass pump, and minimizing the risk of associated complications.

The valves can be placed in any location that allows the control of blood flow to the atrium from the pulmonary veins and prevents or minimizes back flow. The valves could be placed in the pulmonary veins. This offers advantages for percutaneous placement because the system would use multiple valves of smaller diameter. The valves could also be placed inside the atrium this offers the advantage of possibly implanting larger valves that could control the flow of blood from one or more pulmonary vein. The valves could also be positioned in the ostium of the pulmonary veins; this provides similar advantages to implanting the valves in the pulmonary veins but has the advantage that the tissue may be easier to secure the device to. The valve or valves could also be located outside the heart and the blood flow routed through the valve or valves in a prosthetic conduit.

Entry Vessel

In the percutaneous procedure access to the pulmonary veins may be gained by a puncture into the venous system and a trans-septal puncture from the right atrium into the left atrium. In this case access to the venous system is gained by a puncture into a vein, preferably the internal jugular vein or the femoral vein would be used, but other veins are also suitable.

Alternatively in the percutaneous procedure access to the pulmonary veins may be gained, by a puncture into the arterial system. In this case the puncture is preferably performed in the femoral radial or brachial artery although other arteries may be used as well. The catheter is then advanced into the aorta, past the aortic valve, past the mitral valve and into the left atrium where it can access the pulmonary veins Imaging/Monitoring During the procedure or during patient selection, or follow-up, various imaging techniques can be used. These include fluoroscopy, chest x-ray, CT scan and MRI.

During the procedure or during patient selection, or follow-up, various flows and pressures may be monitored, or example echocardiography may be used to monitor the flow of blood through the pulmonary veins, and other chambers and conduits of the coronary system. It may be especially important to visualize regurgitant flow in the pulmonary veins and past the mitral valve. Additionally pressures may be monitored in various chambers and conduits of the heart; for example pulmonary wedge pressure may be an important measurement.

On or Off Pump

The surgical procedure may be performed on a cardiac bypass pump. This would allow the device to be implanted with the heart stopped and may not require a cross-clamp of the pulmonary vein. Alternatively using some of the devices and concepts described the surgical procedure may be performed off pump. While maintaining a beating heart, the operation may be performed by using a cross-clamp method to isolate a pulmonary vessel using two clamps to halt the blood flow between the site implantation. A slit or incision may then be made to insert the valve device into the vessel. Alternatively, a complete separation of the vessel between the two clamps and exposing the lumen could be made to implant the valve device. Both techniques would require a suture or reattachment of the vessel post implantation and a suture or other means may be required to maintain proper valve location within the vessel. The techniques of implantation of the device would apply to on-pump implants as well.

Second Atrium

In an alternative surgical procedure, preferably performed on a beating heart. This procedure utilizes a device that consists of a conduit approximately 20 mm in diameter and a prosthetic valve located in the conduit. The end of the conduit that allows out flow is grafted into the left ventrical. The one-way valve prevents blood from escaping. The pulmonary veins are then transplanted from the left atrium to the inlet side of the conduit. The small portion of the pulmonary veins remaining on the atrium are closed surgically.

What is claimed is:

1. A flow control valve dimensioned for implantation in a human heart, the valve comprising a stentless tubular annular support structure having a first inflatable ring at a proximal end of the support structure, a second inflatable ring at a distal end of the support structure, an annular body extending from the distal end to the proximal end, and an inflatable intermediate support in between the first and second inflatable rings, the intermediate support disposed around the circumference of the tubular support structure and at least one moveable occluder positioned within the stentless tubular annular support that controls the flow of blood through the stentless tubular support structure, wherein introduction of inflation media into the first inflatable ring, the second inflatable ring and inflatable intermediate support structure converts the tubular annular support structure from a first collapsed configuration for translumenal navigation to a second patent tubular configuration.

2. A flow control valve dimensioned for implantation in a human heart as in claim 1, wherein the intermediate support comprises a zig-zag configuration.

3. A flow control valve dimensioned for implantation in a human heart as in claim 1, wherein the occluder comprises tissue.

4. A flow control valve dimensioned for implantation in a human heart as in claim 1, wherein the occluder comprises a synthetic leaflet.

5. A flow control valve dimensioned for implantation in a human heart as in claim 1, further comprising a valve on the support structure for preventing escape of inflation media.

* * * * *

UNITED STATES PATENT AND TRADEMARK OFFICE
CERTIFICATE OF CORRECTION

| | | |
|---|---|---|
| PATENT NO. | : 7,641,686 B2 | Page 1 of 1 |
| APPLICATION NO. | : 11/112847 | |
| DATED | : January 5, 2010 | |
| INVENTOR(S) | : Lashinski et al. | |

It is certified that error appears in the above-identified patent and that said Letters Patent is hereby corrected as shown below:

In column 2, line 31, Change "cardiomyopothies." to --cardiomyopathies--.

In column 3, line 4 (Approx.), Change "floropolymers" to --fluoropolymers--.

In column 5, line 25, Change "transeptal" to --transseptal--.

In column 5, line 50-51, Change "transeptal" to --transseptal--.

In column 5, line 61, Change "tortuerosity" to --tortuosity--.

In column 10, line 51, Change "wayvalve" to --way valve--.

In column 11, line 30, Change "thorascope." to --thoracoscope.--.

In column 12, line 62, Change "ellgilloy" to --elgiloy--.

In column 14, line 46 (Approx.), Change "cardiopeiegic" to --cardioplegic--.

In column 15, line 15, After "veins" insert --.--.

In column 16, line 31 (Approx.), In Claim 1, change "translumenal" to --transluminal--.

Signed and Sealed this
Twenty-seventh Day of September, 2011

David J. Kappos
*Director of the United States Patent and Trademark Office*